United States Patent
Jones et al.

(10) Patent No.: US 11,103,659 B2
(45) Date of Patent: Aug. 31, 2021

(54) DELIVERY DEVICE AND RELATED METHODS

(75) Inventors: Andrew Jones, Rosindale, MA (US);
Richard L. Miller, Needham, MA (US)

(73) Assignee: MANTA DEVICES, LLC, Cambridge, MA (US)

( * ) Notice: Subject to any disclaimer, the term of this patent is extended or adjusted under 35 U.S.C. 154(b) by 1513 days.

(21) Appl. No.: 13/541,261

(22) Filed: Jul. 3, 2012

(65) Prior Publication Data
US 2013/0008442 A1    Jan. 10, 2013

Related U.S. Application Data

(60) Provisional application No. 61/504,843, filed on Jul. 6, 2011.

(51) Int. Cl.
*A61M 15/00* (2006.01)

(52) U.S. Cl.
CPC .... *A61M 15/0028* (2013.01); *A61M 15/0035* (2014.02); *A61M 2202/064* (2013.01); *A61M 2206/16* (2013.01)

(58) Field of Classification Search
CPC .......... A61M 15/0005; A61M 15/0008; A61M 15/0045; A61M 15/005; A61M 15/006; A61M 15/0066; A61M 15/0091; A61M 15/0093; A61M 15/0065; A61M 15/0086
USPC .......................... 128/203.15, 203.19, 203.21
See application file for complete search history.

(56) References Cited

U.S. PATENT DOCUMENTS

| | | |
|---|---|---|
| 2,307,986 A | 1/1943 | Bolte et al. |
| 2,860,638 A | 11/1958 | Bartolomeo |
| 2,974,787 A | 3/1961 | Cooper |
| 3,888,253 A | 6/1975 | Watt et al. |
| 2,893,392 A | 6/1976 | Gerstel et al. |
| 4,249,526 A | 2/1981 | Dean et al. |
| 4,338,931 A | 7/1982 | Cavazza |
| 4,601,896 A | 7/1986 | Nugent |
| 5,035,237 A | 7/1991 | Newell et al. |
| 5,167,242 A | 12/1992 | Turner et al. |
| 5,239,993 A | 8/1993 | Evans |
| 5,320,714 A | 6/1994 | Brendel |
| 5,388,572 A | 2/1995 | Mulhauser et al. |

(Continued)

FOREIGN PATENT DOCUMENTS

| | | |
|---|---|---|
| DE | 4400083 A1 | 7/1995 |
| EP | 0407276 | 1/1991 |

(Continued)

OTHER PUBLICATIONS

Partial International Search Report from related International Application No. PCT/US2008/008303 dated Dec. 4, 2008.

(Continued)

*Primary Examiner* — LaToya M Louis

(74) *Attorney, Agent, or Firm* — Grossman, Tucker, Perreault & Pfleger, PLLC

(57) ABSTRACT

A dose delivery device with a mouthpiece having an inlet, an outlet, and an air path extending between the inlet and the outlet. A dose chamber having an opening may hold a dose, e.g., for inhalation by a user. One or more bypass inlets, two or more dispersion chambers, and/or flow arrangements in which incoming and outgoing flow in a dispersion chamber are transverse may be used to disperse a dose for delivery to a user.

23 Claims, 13 Drawing Sheets

(56) References Cited

U.S. PATENT DOCUMENTS

| | | | |
|---|---|---|---|
| 5,400,808 A | 3/1995 | Turner et al. | |
| 5,476,093 A | 12/1995 | Lankinen | |
| 5,501,236 A | 3/1996 | Hill et al. | |
| 5,562,918 A | 10/1996 | Stimpson | |
| 5,596,982 A | 1/1997 | Blaha-Schnabel | |
| 5,622,166 A | 4/1997 | Eisele et al. | |
| 5,647,349 A | 7/1997 | Ohki et al. | |
| 5,669,378 A | 9/1997 | Pera et al. | |
| 5,673,793 A | 10/1997 | Seidler | |
| 5,752,505 A * | 5/1998 | Ohki et al. | 128/203.15 |
| 5,775,320 A | 7/1998 | Patton et al. | |
| 5,893,452 A | 4/1999 | De Nervo | |
| 5,921,237 A | 7/1999 | Eisele et al. | |
| 5,947,117 A | 9/1999 | Herold | |
| 5,954,204 A | 9/1999 | Grabowski | |
| 6,029,663 A | 2/2000 | Eisele et al. | |
| 6,089,228 A | 7/2000 | Smith et al. | |
| 6,119,688 A * | 9/2000 | Whaley et al. | 128/203.15 |
| 6,209,538 B1 | 4/2001 | Casper et al. | |
| 6,230,707 B1 | 5/2001 | Horlin | |
| 6,234,169 B1 | 5/2001 | Bulbrook et al. | |
| 6,328,034 B1 | 12/2001 | Eisele et al. | |
| 6,347,629 B1 | 2/2002 | Braithwaite | |
| 6,401,712 B1 | 6/2002 | Von Schuckmann | |
| 6,427,688 B1 | 8/2002 | Ligotke et al. | |
| 6,443,152 B1 | 9/2002 | Lockhart et al. | |
| 6,443,307 B1 | 9/2002 | Burridge | |
| 6,449,688 B1 * | 9/2002 | Peters et al. | 711/112 |
| 6,550,477 B1 | 4/2003 | Casper et al. | |
| 6,595,203 B1 | 7/2003 | Bird | |
| 6,595,210 B2 | 7/2003 | Ohki et al. | |
| 6,655,381 B2 | 12/2003 | Keane et al. | |
| 6,681,768 B2 | 1/2004 | Haaije de Boer et al. | |
| 6,748,947 B2 | 6/2004 | Keane et al. | |
| 6,810,872 B1 | 11/2004 | Ohki et al. | |
| 6,871,646 B2 | 3/2005 | Keane et al. | |
| 6,932,082 B2 | 8/2005 | Stein | |
| 6,941,947 B2 | 9/2005 | Young et al. | |
| 6,971,384 B2 | 12/2005 | Gieschen et al. | |
| 7,025,056 B2 | 4/2006 | Eason et al. | |
| 7,025,057 B2 | 4/2006 | Chawla | |
| 7,143,765 B2 | 12/2006 | Asking et al. | |
| 7,401,713 B2 | 7/2008 | Ede et al. | |
| 7,617,822 B2 | 11/2009 | De Boer et al. | |
| 7,854,227 B2 * | 12/2010 | Djupesland | 128/203.18 |
| 8,109,267 B2 | 2/2012 | Villax et al. | |
| 2001/0027790 A1 | 10/2001 | Gieschen et al. | |
| 2001/0029948 A1 | 10/2001 | Ingle et al. | |
| 2002/0006316 A1 | 1/2002 | Schuler et al. | |
| 2002/0020408 A1 | 2/2002 | Knauer | |
| 2002/0073997 A1 * | 6/2002 | Keane et al. | 128/203.21 |
| 2002/0092523 A1 | 7/2002 | Connelly et al. | |
| 2002/0170560 A1 | 11/2002 | Young et al. | |
| 2003/0034271 A1 | 2/2003 | Burridge | |
| 2004/0107963 A1 | 6/2004 | Finlay et al. | |
| 2004/0182387 A1 | 9/2004 | Steiner et al. | |
| 2004/0206350 A1 | 10/2004 | Alston et al. | |
| 2004/0211419 A1 | 10/2004 | Eason et al. | |
| 2004/0236282 A1 | 11/2004 | Braithwaite | |
| 2005/0022813 A1 | 2/2005 | Alston | |
| 2005/0188988 A1 | 9/2005 | Poole et al. | |
| 2006/0005833 A1 | 1/2006 | Gieschen et al. | |
| 2006/0108877 A1 | 5/2006 | Tegel | |
| 2006/0169278 A1 | 8/2006 | Djupesland et al. | |
| 2007/0023381 A1 | 2/2007 | Cerveny | |
| 2007/0074721 A1 | 4/2007 | Harmer et al. | |
| 2007/0151562 A1 | 7/2007 | Jones et al. | |
| 2007/0283955 A1 * | 12/2007 | Tsutsui | 128/203.15 |
| 2008/0251072 A1 | 10/2008 | Lulla et al. | |
| 2008/0314384 A1 | 12/2008 | Harris et al. | |
| 2009/0013994 A1 * | 1/2009 | Jones et al. | 128/200.23 |
| 2009/0250057 A1 | 10/2009 | Wachtel | |
| 2009/0308392 A1 | 12/2009 | Smutney et al. | |
| 2009/0321295 A1 | 12/2009 | Ede et al. | |
| 2010/0006096 A1 * | 1/2010 | Kakade | 128/203.15 |

FOREIGN PATENT DOCUMENTS

| | | |
|---|---|---|
| EP | 1844809 A1 | 10/2007 |
| GB | 1211168 A | 11/1967 |
| GB | 2179260 A | 3/1987 |
| GB | 2375310 A | 11/2002 |
| GB | 2405798 A | 3/2005 |
| GB | 2420982 A | 6/2006 |
| JP | 08-103499 A | 4/1996 |
| WO | WO 90/07351 A1 | 7/1990 |
| WO | WO 96/09085 | 3/1996 |
| WO | WO 99/06092 A1 | 2/1999 |
| WO | WO 01/05675 A1 | 1/2001 |
| WO | WO 01/26720 A1 | 4/2001 |
| WO | WO 01/56640 A1 | 9/2001 |
| WO | WO 01/85097 | 11/2001 |
| WO | WO 02/098495 A1 | 12/2002 |
| WO | WO 03/000326 A1 | 1/2003 |
| WO | WO 03/015857 A1 | 2/2003 |
| WO | WO 2004/103446 A1 | 12/2004 |
| WO | WO 2005/002654 A3 | 1/2005 |
| WO | WO 2005/025656 A1 | 3/2005 |
| WO | WO 2005/030305 A1 | 4/2005 |
| WO | WO 2006/066910 A1 | 6/2006 |
| WO | WO 2007/007110 A1 | 1/2007 |
| WO | WO 09/092650 | 7/2009 |

OTHER PUBLICATIONS

International Preliminary Report on Patentability from related International Application No. PCT/US2010/000090 dated Jul. 19, 2011.

* cited by examiner

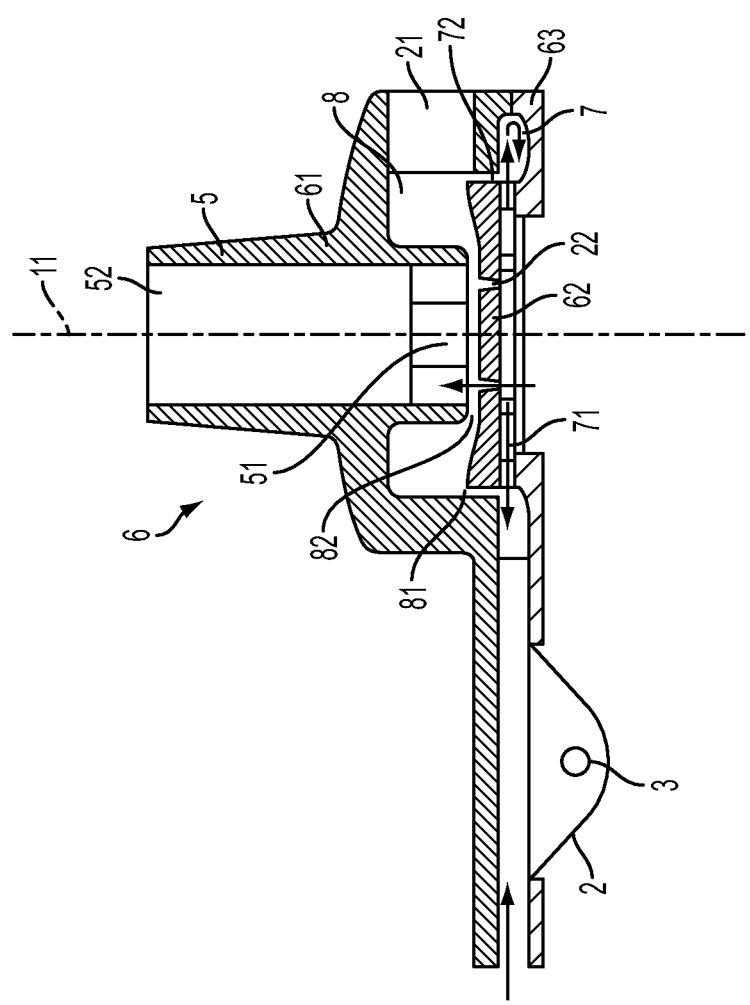

DELIVERY DEVICE AND RELATED METHODS

This application claims the benefit of U.S. Provisional application No. 61/504,843, filed Jul. 6, 2011, which is hereby incorporated in its entirety.

BACKGROUND

Medicament in the form of dry powder may be delivered directly into the lungs, such as by inhalation. Administering medicament in this manner may prove less invasive than other drug delivery techniques, such as hypodermic injections. Direct inhalation of medicament may also allow smaller doses to be used to achieve results similar to those of the same drug taken orally. Inhalation may also help avoid undesirable side effects associated with administering drugs orally or by injection.

SUMMARY OF INVENTION

Aspects of the invention relate to devices, systems, and methods that are used to deliver a dose of a powder, such as a medicament, a flavorant, or another substance. The devices, systems and methods may include features that allow the dose to be protected (e.g., from contamination and/or degradation) prior to use, and to be delivered in a metered manner. For example, in some embodiments, the dose is isolated to a selected volume/dose chamber by a barrier, such as a foil layer around the dose chamber or the entire delivery device that prevents the ingress of contaminants and/or the egress of a dose from the dose chamber prior to use. As a result, the initial location of the drug dose may be known, and the dose may be delivered from the device in a consistent and predictable manner.

In one aspect of the invention, a dose delivery device includes a housing having an inlet at a first end, an outlet at a second end, and an air path extending between the inlet and the outlet. In one arrangement, the inlet and outlet may be associated with a mouthpiece portion of the housing and arranged to deliver dose entrained air to a user at the outlet. The device may also include a first chamber having an inlet and an outlet and arranged so that fluid flowing in the first chamber in an outlet direction to the first chamber outlet is transverse to, and crosses, fluid entering the first chamber via the first chamber inlet. Such a crossing of inlet and outlet flows in the first chamber may help disperse the dose in the first chamber, e.g., by causing the breakdown of particles in the outlet flow and/or helping retain particles over a particular size in the first chamber. A second chamber of the device may have an inlet arranged to receive dose entrained air from the first chamber outlet, and an outlet fluidly coupled to the housing to provide dose entrained air to the housing inlet. The second chamber, like the first chamber, may be arranged to disperse dose in the dose entrained air provided to the housing inlet. A bypass inlet may be arranged to introduce air into the second chamber in a generally radially inward direction. Thus, the bypass air may help generate a circulatory flow in the second chamber, which may be useful for dispersing dose by causing turbulence in the second chamber, causing dose particles to impact the chamber wall and/or lowering a concentration of the dose in the flow. A dose chamber may also be provided to hold a dose. The dose chamber may be incorporated as part of the first chamber, the second chamber and/or as a separate chamber.

In some embodiments, fluid flowing in the outlet direction in the first chamber may contact fluid flowing in the inlet direction into the first chamber. This contact of flows may help with dose dispersion by the physical contact of air with dose particles (which may break the particles down in size), and/or by the incoming air pushing larger, higher drag particles into contact with the first chamber walls or otherwise retaining larger dose particles in the first chamber. In other embodiments, a stream of fluid flowing in the outlet direction may pass between a pair of streams of fluid flowing in the inlet direction. This type of flow arrangement may help with dose dispersion by, for example, creating turbulence in the outgoing flow. The inlet direction of flow into the first chamber need not be a single linear direction, but may include one or more flows that define a portion of a plane or other two dimensional surface. For example, flow into the first chamber, which may have a toroidal shape, may occur through an annular or hoop-shaped space.

In some embodiments, the first chamber may define the dose chamber. Thus, the first chamber inlet and outlet may be selectively openable and closable, e.g., to allow a user to open the first chamber immediately prior to use to release the dose for delivery to the user. The first chamber may have any suitable shape, such as a toroidal shape, a cylindrical shape, a conical shape, etc., and may be arranged to cause flow in the first chamber to follow a spiral or helical path. For example, flow in the first chamber may not only circulate circumferentially around the first chamber, but may also follow a spiral or helical path around the first chamber. Such spiral or helical flow may be driven, at least in part, by fluid entering a toroidally-shaped first chamber in a radially outwardly direction relative to the toroidal shape, and fluid exiting the first chamber in an axial direction relative to the toroidal shape.

In some embodiments, the second chamber may have a cylindrical shape, and the second chamber and the bypass inlet may be arranged to produce a circulating flow in the second chamber. Thus, both the first and second chambers may have a circulating flow, which has been found to be useful in dispersing a dose. In one arrangement, the bypass inlet may be arranged to admit air into the second chamber in a direction tangential to flow in the second chamber. The tangential introduction of air into the second chamber may help to drive the circulatory flow, as well as have other effects, such as creating turbulence in the flow. The flow of air via the bypass inlet may be in a generally inward direction into the second chamber, or in an outward direction.

Dose entrained air exiting from the first chamber may enter into the second chamber near a periphery of the cylindrical shape, e.g., at the outer periphery and along a longitudinal axis of a cylindrical shape of the second chamber. This arrangement may help encourage contact between air admitted by the bypass inlet into the second chamber and the dose entrained air from the first chamber, helping to disperse the dose. In one arrangement, centers of the toroidal shape of the first chamber and the cylindrical shape of the second chamber are arranged along a longitudinal axis of the device, and the second chamber outlet may be located near the longitudinal axis. Thus, the first and second chambers may be stacked and arranged so that outflow from the second chamber occurs along a longitudinal axis of the device, allowing for easy supply of dose entrained air to a user. Additionally, there may be a bypass pathway arranged along the longitudinal axis, and a second bypass inlet may admit air into the second chamber in a direction along the longitudinal axis. The air admitted by the second bypass inlet may help to further disperse the dose, and/or help direct dose entrained air exiting the second chamber to flow in a desired direction into the device inlet.

In another aspect of the invention, a dose delivery device includes a housing having an inlet at a first end, an outlet at a second end, and an air path extending between the inlet and the outlet. The device may also include a first chamber having an outlet arranged to provide a dose at the first chamber outlet. A second chamber of the device may have a cylindrical shape, an inlet arranged to receive dose from the first chamber outlet, and an outlet fluidly coupled to the housing to provide dose entrained air to the housing inlet. Fluid entering the second chamber via the second chamber inlet may be arranged in a direction along a longitudinal axis of the cylindrical shape and located near a periphery of the cylindrical shape. One or more bypass inlets may be arranged to provide air into the second chamber, and the bypass inlets may be separate from the second chamber inlet. For example, the second chamber inlet may be arranged to receive dose entrained fluid around a periphery of the cylindrical shape, and a bypass inlet may admit air into the cylindrical shape generally inwardly and/or tangentially to flow at the outer peripheral side of the cylindrical shape. As discussed above, this feature may help to disperse the dose in the second chamber, e.g., by having the dose entrained flow intersect with the bypass air and using a circulatory flow in the second chamber.

In one embodiment, the first chamber has a toroidal shape, and is arranged to hold the dose and provide dose entrained air at the first chamber outlet. The first chamber may include an air inlet and the first chamber inlet and outlet may be selectively openable and closable. Also, the first chamber may have a larger diameter than the second chamber, e.g., so that dose entrained air exiting at a radially inner wall of the first chamber enters at a radially outer wall of the second chamber. In one embodiment, the larger diameter first chamber may be arranged to meter larger size particles than the second chamber. For example, the first chamber may be arranged to meter particles having a size of about 15 microns, whereas the second chamber is designed to meter particles having a size of about 5 microns or less. Such an arrangement may be useful, for example, where the first chamber is arranged to breakdown dose particles to a particular size or size range (such as about 15 microns), and then pass the particles to the second chamber for further breakdown and later introduction to the housing air flow path for delivery to a user.

In another aspect of the invention, a dose delivery device includes a housing having an inlet at a first end, an outlet at a second end, and an air path extending between the inlet and the outlet. The device may also include a first chamber having an outlet arranged to provide a dose at the first chamber outlet. A second chamber may have an inlet arranged to receive dose from the first chamber outlet, and an outlet fluidly coupled to the housing to provide dose entrained air to the housing inlet. In addition, the second chamber may include a concave depression opposite the housing inlet that optionally includes at least one opening to direct bypass air into the second chamber and toward the housing inlet. The concave depression may help create a tortuous or otherwise curved path for flow in the second chamber to help disperse dose and prevent unsuitably large dose particles from exiting the second chamber. Moreover, the bypass air admitted into the second chamber opposite the housing inlet may help further disperse dose, e.g., by creating a shearing flow, turbulence, physical contact with dose particles, reducing dose concentration, reducing dose sedimentation in a flow straightener downstream of the second chamber (if present), etc.

Similar to alternate embodiments discussed above, the second chamber may have a cylindrical shape, and the concave depression may be located near a center of the cylindrical shape. In one arrangement, the housing inlet protrudes into the second chamber and toward the concave depression. This protrusion of the housing inlet may provide a wall or other barrier to help prevent unsuitably large dose particles from exiting the second chamber, e.g., by forcing a curved flow path for dose entrained air to exit the second chamber. The second chamber inlet may also be arranged to receive dose entrained fluid around a periphery of the cylindrical shape of the second chamber. Thus, with the second chamber outlet located near a center of the cylindrical shape, dose may be forced to flow toward a center of the second chamber to exit to the housing inlet. In the presence of a circulating flow in the second chamber, larger dose particles may be effectively prevented from exiting the second chamber, e.g., because of a lack of suitably large force (e.g., caused by aerodynamic drag of air moving to the second chamber outlet) to move the circulating particles to the center of the second chamber for exit. A bypass inlet may be provided to direct air in a radially inward direction into the second chamber, e.g., that is tangential to flow in the chamber and produce a circulating flow in the second chamber. In some cases, the second chamber inlet and the bypass inlet may be arranged such that dose entrained air entering the second chamber inlet intersects with air entering via the bypass inlet.

In one embodiment, the first chamber has a toroidal shape, and is arranged to hold the dose and provide dose entrained air at the first chamber outlet. The first chamber may include an air inlet and the first chamber inlet and outlet may be selectively openable and closable. Also, the first chamber may have a larger diameter than the second chamber, e.g., so that dose entrained air exiting at a radially inner wall of the first chamber enters at a radially outer wall of the second chamber. Flow in the first chamber may follow a spiral path, e.g., with fluid entering the first chamber via a first chamber inlet moving radially outwardly relative to the toroidal shape, and fluid exiting the first chamber moving axially relative to the toroidal shape.

In another aspect of the invention, a dose delivery device includes a housing having an inlet at a first end, an outlet at a second end, and an air path extending between the inlet and the outlet. The device may also include a first chamber having an outlet arranged to provide a dose at the first chamber outlet, and a second chamber having an inlet arranged to receive dose from the first chamber outlet, and an outlet fluidly coupled to the housing to provide dose entrained air to the housing inlet. A first bypass inlet may be arranged to admit air into the second chamber near the second chamber inlet such that fluid flow from the first chamber outlet into the second chamber inlet is transverse to and intersects with air admitted by the first bypass inlet. For example, where the second chamber has a cylindrical shape, the second chamber inlet may be arranged such that fluid entering the second chamber via the second chamber inlet is arranged in a direction along a longitudinal axis of the cylindrical shape whereas air admitted by the first bypass inlet is admitted perpendicular to the longitudinal axis of the cylindrical shape. Also, a second bypass inlet may be arranged to admit air into the second chamber near the second chamber outlet such that fluid flow from the second chamber outlet into the housing inlet is generally transverse to and intersects with air admitted by the second bypass inlet. By providing bypass air into the second chamber in two locations, at the inlet to the second chamber and the outlet from the second chamber, in a way that intersects with dose entrained flow, excellent dose dispersion can be achieved.

In one embodiment, the first chamber has a toroidal shape with a center, the second chamber has a cylindrical shape with a center, and the centers of the toroidal shape and the cylindrical shape are located along an air path of the second bypass inlet. Moreover, the air path of the second bypass inlet may be generally parallel to the air path extending between the housing inlet and the housing outlet. Thus, the first and second chambers may be stacked with at least some bypass flow and the main outlet flow occurring along a longitudinal axis of the chambers and of the device. The first bypass inlet and the second chamber may be arranged to form a spiral flow of dose entrained air in the second chamber, e.g., the first bypass inlet may introduce air generally inwardly into the second chamber and in a direction that is tangential to flow in the second chamber. The second chamber may also have a concave depression located near a center of a cylindrical shape of the chamber, e.g., where air introduced via the second bypass inlet enters the concave depression. (While in this illustrative embodiment, the first and second chambers may be stacked, one on the other, it is possible in other embodiments to have the first and second chambers arranged side-by-side (whether in a same or parallel planes), in transverse planes (e.g., with one chamber in a plane perpendicular to the other), and so on.

In another aspect of the invention, a dose delivery device includes a housing having an inlet at a first end, an outlet at a second end, and an air path extending between the inlet and the outlet. The device may also include a first chamber having a toroidal shape arranged to disperse a dose in a fluid flow in the first chamber, an inlet, and an outlet fluidly coupled to the housing to provide dose entrained air to the housing inlet. The first chamber inlet may be arranged radially inwardly of the first chamber outlet and near a top surface of the toroidal shape which is located nearer the housing inlet than a bottom surface of the toroidal shape. Such an arrangement may not only induce a circulatory flow in the first chamber, e.g., such that fluid entering via the first chamber inlet is caused to flow radially outwardly toward an outer periphery of the first chamber, along the outer periphery of the first chamber away from the first chamber outlet, and radially inwardly toward the first chamber outlet, but also to cause interaction between the inlet and outlet flows so that fluid flowing in an outlet direction from the first chamber outlet is transverse to, and crosses, fluid flowing into the first chamber via the first chamber inlet in an inlet direction.

In one embodiment, a peripheral outer surface of the toroidal shape is generally transverse to a direction of fluid flow at the first chamber inlet, which may cause dose in the first chamber to strike the outer peripheral wall and be broken down in size. Other embodiments may include additional features discussed above, such as a second chamber that receives dose entrained air from the first chamber and disperses the dose further, various bypass inlets to cause circulatory flow, turbulence or other conditions to assist in dose dispersal, and so on.

In another aspect of the invention, a dose delivery device includes a housing having an inlet at a first end, an outlet at a second end, and an air path extending between the inlet and the outlet. A first chamber may have an inlet and an outlet fluidly coupled to the housing to provide dose entrained air to the housing inlet (e.g., via a second chamber or other flow path). Fluid entering the first chamber via the first chamber inlet may be arranged in a generally radially outward direction, and the first chamber, the first chamber inlet and the first chamber outlet may be arranged such that fluid entering via the first chamber inlet is caused to flow radially outwardly toward an outer periphery of the first chamber, along the outer periphery of the first chamber away from the first chamber outlet, and radially inwardly toward the first chamber outlet. This type of circulatory flow may be augmented by circumferential circulatory flow around the first chamber, e.g., where the first chamber has a toroidal shape. Circumferential circulatory flow may be induced by an arrangement of the first chamber inlet and/or other features.

In one embodiment, fluid flowing from the bottom of the first chamber toward the first chamber outlet may be transverse to, and cross, fluid flowing into the first chamber from the first chamber inlet. This arrangement may cause the outlet and inlet flows to intersect or collide with each other. A dose may be located in the first chamber, or may be provided from another source. A second chamber, e.g., having a cylindrical shape, may receive fluid from the first chamber, and provide fluid to the housing inlet. Other embodiments may include additional features discussed above, such as various bypass inlets to cause circulatory flow, turbulence or other conditions to assist in dose dispersal, a stacked arrangement of a first and second chamber, and so on.

In another aspect of the invention, a dose delivery device may be arranged such that dose entrained flow passing from one dispersion chamber to another, or from a dose chamber to a dispersion chamber, or from a dispersion chamber to a device outlet may be exposed to transverse bypass air flow. For example, flow from a first dispersion chamber to a second dispersion chamber, and flow from the second dispersion chamber to the device outlet may be exposed to bypass air flow to help disperse the dose and/or provide other dose delivery characteristics (such as straightened flow at the device outlet). The flow paths between dispersion chambers or other device sections may be relatively short and exposed to bypass air flows at their outlets, e.g., to help reduce sedimentation or provide other dispersion characteristics.

Aspects of the invention can be used in any suitable arrangement, including dose delivery device that are usable a single time with a single dose chamber, and including a dose delivery device that is usable multiple times with multiple dose chambers. For example, dose delivery device may include a plurality of dose chambers arranged in a multi-dose chamber configuration in which each dose chamber can be serially opened and used to deliver a dose to a user.

Other aspects, features and advantages will be apparent from the description of the following embodiments and from the claims.

BRIEF DESCRIPTION OF THE DRAWINGS

Illustrative embodiments of the invention are more particularly described in the following detailed description, taken in conjunction with the accompanying drawings. In the drawings, like reference characters generally refer to the same parts throughout the different views. Also, the drawings are not necessarily to scale, emphasis instead generally being placed upon illustrating principles of the invention.

FIG. 3 shows a cross sectional view of a dose delivery device in which a dose chamber is associated to a side of the device;

DETAILED DESCRIPTION

Delivery devices described herein include one or more dose chambers for storing and delivering a dose of a substance, such as a powdered medicament, including blended formulations, excipient formulations, neat formulations or combinations thereof, a flavorant, etc., to a subject. The dose chamber may be placed in fluid communication with an air pathway to ready the dose for delivery to the subject. Air may be drawn and/or pushed through the air pathway and at least a portion of the air that enters the dose chamber may entrain the dose in a metered manner. Dose entrained air may move along an air pathway from the dose chamber, laden with powder from the dose chamber towards an outlet of the delivery device to a subject.

Figure 2:
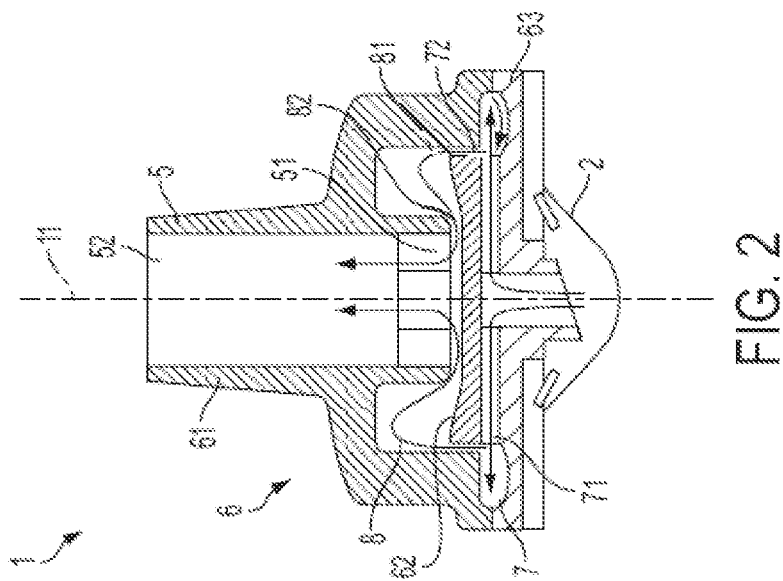
FIGS. 1 and 2 show cross sectional views of a dose delivery device prior to association with a dose chamber and after association with a dose chamber, respectively.
Figure 1:
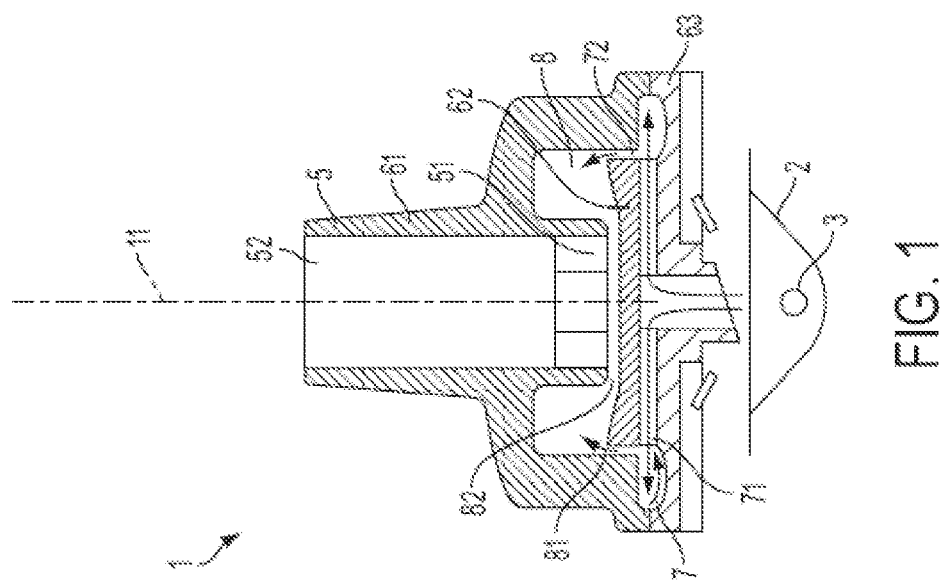

FIGS. 1 and 2 show a cross sectional side view of a dose delivery device 1 that incorporates one or more aspects of the invention. In this illustrative embodiment, a dose 3 which is initially contained in a dose chamber 2, is metered or otherwise dispersed in an air flow that passes through first and second dispersion chambers 7 and 8, and to the outlet 52 of a mouthpiece 5. (Although in this embodiment, the mouthpiece 5 is generally straight, the mouthpiece 5 and an associated flow path may include a right angle or any other suitable bend or orientation.) While the dose 3 may be provided to the delivery device 1 in any suitable way (several of which are discussed in detail below), in this embodiment, a lower housing portion 63 of the device 1 is arranged to pierce the dose chamber 2 (which may be formed by a pair of foil or other barrier layers that are joined together to enclose the dose 3) by a tubular spike or multiple spikes that define an inlet to receive dose 3. Inhalation of a user through the mouthpiece 5 may draw air into the dose chamber 2, which causes dose to be entrained into the air that then flows into the first chamber 7. The dose 3 may move from the dose chamber 2 to the first chamber 7 in a bulk fashion, or may be metered from the dose chamber 2 to the first chamber 7. A swirling or other flow pattern in the first chamber 7 may help disperse and meter the dose into the air flow, e.g., by breaking particles of the dose 3 into suitably small size and distributing the particles into the air flow. Dose entrained air that exits the first chamber 7 via the first chamber outlet 72 may enter the second chamber 8 via a second chamber inlet 81. In this embodiment, the first chamber outlet 72 and the second chamber inlet 81 are connected by an annular shaped space, but may be fluidly coupled in any suitable way, such as by one or more separate flow paths. For example, the first chamber outlet 72 may function as a flow straightener (e.g., include a plurality of straight pathways that cause flow to move in a single common direction), can be arranged to induce a swirling or other flow in the second chamber 8, can function to help further disperse dose before passing the dose to the second chamber 8, may include bypass or other inlets to introduce air into the flow in the first chamber outlet 72, and so on. A swirling or other flow pattern in the second chamber 8 may help to further disperse the dose 3, which may exit the second chamber 8 at a second chamber outlet 82 and pass into an inlet 51 of the mouthpiece 5.

While the delivery device 1 may be constructed in any suitable way, including any suitable number or other arrangement of parts, in this embodiment, the delivery device 1 includes a housing 6 that has an upper housing portion 61, a lower housing portion 63 and a middle housing portion 62. These three portions of the housing 6 define the first and second chambers 7, 8, the mouthpiece 5, and other portions of the device 1 apart from the dose chamber 2. However, other arrangements are possible, such as having one or more portions of the housing 6 define a dose chamber 2.

One aspect of the invention included in the FIGS. 1 and 2 embodiment is that the dose delivery device includes a housing having an inlet at a first end (e.g., the mouthpiece inlet 51), an outlet at a second end (e.g., the mouthpiece outlet 52), and a first chamber with a toroidal shape arranged to disperse a dose in a fluid flow that is provided to the housing inlet. In accordance with this aspect of the invention, the first chamber has an inlet (e.g., the first chamber inlet 71) that is arranged radially inwardly of the first chamber outlet (e.g., the first chamber outlet 72) and near top surface of the toroidal shape which is located nearer the housing inlet than a bottom surface of the toroidal shape. As used herein, "toroidal" is used to refer to a shape that is generally donut-shaped, but it not limited to a shape that has a circular cross section. Instead, a "toroidal" shape may have any suitable cross sectional shape, such as rectangular, elliptical, triangular, or any other regular or irregular polygon, or other irregular shape. Moreover, a "toroidal" shape need not necessarily be symmetrical about any plane or axis, but may have a varying shape. In addition, a toroidal shape need not extend about 360 degrees, may only extend around a central longitudinal axis to an extend less than 360 degrees.

With specific reference to FIGS. 1 and 2, it can be seen that the first chamber inlet 71 is located radially inward of the outlet 72, i.e., closer to the longitudinal axis 11 of the device 1 and the toroidal shape of the first chamber 7 than the outlet 72. In addition, the first chamber inlet 71 is located nearer a top surface of the first chamber 7 than a bottom surface of the first chamber 7. Thus, in accordance with an aspect of the invention, air entering the first chamber 7 may be generally caused to flow radially outwardly toward an outer peripheral surface of the first chamber 7, flow downwardly along the outer peripheral surface away from the first chamber outlet 72, and then flow radially inwardly back toward the longitudinal axis 11 and the first chamber outlet 72. This type of circulating flow may help disperse dose, e.g., by causing the incoming dose entrained fluid to strike the outer peripheral wall of the first chamber 7, causing particles to be broken down in size. Accordingly, in one aspect of the invention, the outer peripheral surface of the toroidal shape (i.e., a wall farthest from the axis 11) may be perpendicular or otherwise generally transverse to the direction of fluid flow at the first chamber inlet 71. This arrangement may help provide an impact surface for dose particles entering the first chamber 7, and an effect of the impact may be enhanced by having the outer peripheral surface be generally flat and parallel to the axis 11. In addition, or alternately, flow in the first chamber 7 may circulate about the longitudinal axis 11, i.e., circumferentially around the toroidal shape. Thus, in some embodiments, flow in the first chamber may follow a spiral or helical path around the toroidal shape.

In accordance with another aspect of the invention, the first chamber inlet and outlet may be arranged such that fluid flowing in an outlet direction to the first chamber outlet is transverse to, and crosses, fluid flowing in an inlet direction into the first chamber via the first chamber inlet. As can be seen in FIGS. 1 and 2, flow in the first chamber circulates so that incoming flow is radially out along the top of the first chamber, down along the outer peripheral wall, radially in along the bottom of the first chamber, and then turns upwardly toward the first chamber outlet 72. As a result, flow moving in the outlet direction to exit the first chamber is transverse to, and crosses, fluid entering the first chamber. This arrangement can provide features such as causing collisions between particles in the incoming fluid flow and the outgoing fluid flow, which may cause improved particle breakdown and dispersion. Also, the crossing of flows in this manner may cause larger particles (e.g., particles with a higher drag) in the outgoing flow to be swept back into the first chamber by the incoming flow. Alternately, or in addition, larger particles may be less capable of making a turn or other movement toward the first chamber outlet 72 than smaller particles, and thus larger particles may remain in the first chamber 7. Moreover, if the delivery device is used in an upright orientation like that shown in FIGS. 1 and 2, the force of gravity may help keep larger, heavier particles from exiting with the outgoing flow. In some arrangements, fluid flowing in the outlet direction may contact fluid flowing in the inlet direction, whereas in other embodiments a stream of fluid flowing in the outlet direction passes between a pair of streams of fluid flowing in the inlet direction. For example, in some arrangements the first chamber inlet 71 may include a plurality of radially oriented channels that lead into the first chamber 7, and the first chamber outlet 72 may include a plurality of axially (e.g., upwardly) oriented channels leading into the second chamber 8. In this arrangement, the inlet and outlet channels may be alternated so that the flows cross each other without substantial contact, whereas in other arrangements, the channels may be arranged to encourage contact. For example, the first chamber inlet 71 may be defined by a fan or turbine blade design that provides for approximately continuously distributed flow into the first chamber around its toroidal shape. In this arrangement, outlet flow to the first chamber outlet 72 may be forced to cross through the inlet flow. It should be understood, therefore, that an "inlet direction" of flow into the first chamber may define a portion of a plane or other surface (e.g., having an annular shape) as opposed to defining a single line. Similarly, the "outlet direction" may include flow along a two dimensional shape, such as a partial cylinder, as well as along a single line or other curve.

The second chamber 8 of the delivery device 1 (if provided) may also function to help disperse dose in an air flow. In this embodiment, the second chamber 8 has a generally cylindrical shape, but like the first chamber can have other forms. In accordance with an aspect of the invention, a center of the toroidal shape of the first chamber and a center of the cylindrical shape of the second chamber may be arranged along the longitudinal axis 11, e.g., so that the first and second chambers 7, 8 are stacked like that shown in FIGS. 1 and 2. In this embodiment, the second chamber outlet 82 is located near the longitudinal axis, whereas the second chamber inlet 81 is located near an outer periphery of the cylindrical shape. The second chamber inlet 81 may be formed by an annular gap between the middle housing portion 62 and the upper housing portion 61, but may have other arrangements, such as a plurality of openings, flow paths or other. Flow in the second chamber 8 may circulate, e.g., around the longitudinal axis 11. Circulatory flow may be induced by the configuration of the second chamber inlet 81 or outlet 82, e.g., the second chamber inlet 81 may introduce flow into the second chamber 8 so as to be tangential to the circulatory flow direction. In other embodiments, a bypass inlet (not shown in this embodiment) may be provided (e.g., in the upper housing portion 61 by multiple openings at the outer periphery of the second chamber 8) to allow air from outside the housing 6 to enter the second chamber. The bypass inlet may be arranged to not only help reduce the dose concentration in the flow, but also to help induce circulatory flow in the second chamber 8, e.g., by admitting air in a direction tangential to the circulatory flow. The direction of flow in the second chamber 8 may be in a same direction as in the first chamber 7, or in an opposite or otherwise different direction. In other embodiments, a bypass inlet may be arranged to admit air into the second chamber in a direction along a longitudinal axis of the second chamber. For example, the middle housing portion 63 may include one or more openings that permit air to flow along the direction of the longitudinal axis 11 and into the second chamber 8.

In accordance with another aspect of the invention, the second chamber includes a concave depression opposite the housing inlet. For example, in FIGS. 1 and 2, the middle housing portion 62 includes a concave depression opposite the mouthpiece inlet 51. The depression may provide a feature of causing flow in the second chamber 8 to follow an "S" shaped path (shown in FIG. 2), helping to trap larger particles in the second chamber and improving the dose dispersion. In addition, the housing inlet (e.g., the mouthpiece inlet 51) may extend or protrude into the second chamber 8, thereby providing a wall or other obstacle to prevent certain dose particles from traveling directly from the second chamber inlet 81 to the housing inlet 51. In some embodiments, the concave depression may include a bypass inlet, e.g., to allow air to enter the second chamber along the direction of the longitudinal axis 11. Such bypass flow may help disperse dose, e.g., by causing the bypass flow to contact the flow exiting the second chamber. However, the concave depression need not include a bypass inlet.

FIG. 3 shows a cross sectional side view of another illustrative embodiment that incorporates one or more aspects of the invention. This embodiment is very similar to that of FIGS. 1 and 2, and those common features are not described again. However, this embodiment includes a first bypass inlet 21 that is arranged to admit air into the second chamber in a generally radially inward direction. In accordance with an aspect of the invention, air entering the second chamber 8 via the first bypass inlet 21 (which may include one or more openings in the upper housing 61 or other suitable components) may intersect with dose entrained fluid flow entering at the second chamber inlet 81, e.g., the first chamber outlet 72 may direct dose entrained flow directly into inflow via the first bypass inlet 21. This intersection of flows may provide features of creating turbulence in the second chamber 8, and/or impacting dose particles in the flow entering at the inlet 81 with a transverse flow, and may help disperse the dose. For example, turbulence in the flow may help to break up dose particles and/or mix clean air with the dose entrained air from the first chamber 7. Impacting of dose particles with incoming clean air may help break up dose particles, either by the contact of clean air with the particles, or by the impact causing the particles to strike wall portions of the second chamber 8. In addition, or alternately, intersection of flows may reduce a volume or flow rate of air that exits the first chamber 7, essentially reducing a total flow through the first chamber 7. Although only one opening is shown as corresponding to the first bypass inlet 21 in FIG. 3, the first bypass inlet 21 may include multiple openings. In addition, the first bypass inlet 21 may be arranged to introduce air into the second chamber 8 in any suitable way, such as in a direction tangential to flow in the second chamber 8. In fact, the first bypass inlet 21 may introduce air so as to induce circulatory flow in the second chamber 8. In addition, bypass inlet openings may be inline with, or staggered relative to second chamber inlet openings, if desired. (Although in this embodiment, only the second chamber includes a bypass inlet, it is possible for the first chamber 7 to have a bypass inlet, e.g., an inlet that provides air into the first chamber 7 in any suitable way, such as though a bottom wall, outer peripheral wall, inner peripheral wall, top wall, or other location of the first chamber 7. This is true for any of the embodiments described herein.)

Another aspect of the invention illustrated in FIG. 3 is a second bypass inlet 22 arranged to admit air into the second chamber 8 such that the admitted air intersects with dose entrained air at the second chamber outlet 82. In this embodiment, the second bypass inlet 22 includes a plurality of openings in the middle housing portion 62 arranged to admit air in a direction along the longitudinal axis 11. Also present in this embodiment is that the air admitted by the second bypass inlet 22 is directed into the second chamber 8 in a direction generally along an air path that extends from the mouthpiece inlet 51 to the outlet 52. Intersection of air admitted by the second bypass inlet 22 with dose entrained flow exiting the second chamber 8 may help disperse the dose, e.g., by creating turbulence, impacting dose particles, and/or reducing a concentration of dose in the flow.

Also present in this embodiment is that dose 3 from a dose chamber 2 may be introduced into the first chamber 7 along a radial pathway in fluid communication with the first chamber 7. The dose chamber 2 may be opened in any suitable way, such as by piercing, breaking, peeling a removable lid from the dose chamber 2 before association with the delivery device 1, etc., to release the dose, and air drawn into the radial pathway may remove dose from the dose chamber 2 and carry the dose to the first chamber 7. As with the FIGS. 1 and 2 embodiment, the delivery device 1 may be arranged to be used with a single dose chamber 2 (e.g., as a single use device), or may be arranged to be used with multiple dose chambers 2 (e.g., in a multi-use device). The dose chamber 2 may be provided as single, separate units, or may be provided in an array, such as a linear strip of dose chambers 2, in a circular array, a rectangular array, etc. Moreover, a single dose chamber 2 (or multiple dose chambers) may feed multiple dispersion chambers, such as the first chamber 7.

Figure 5:
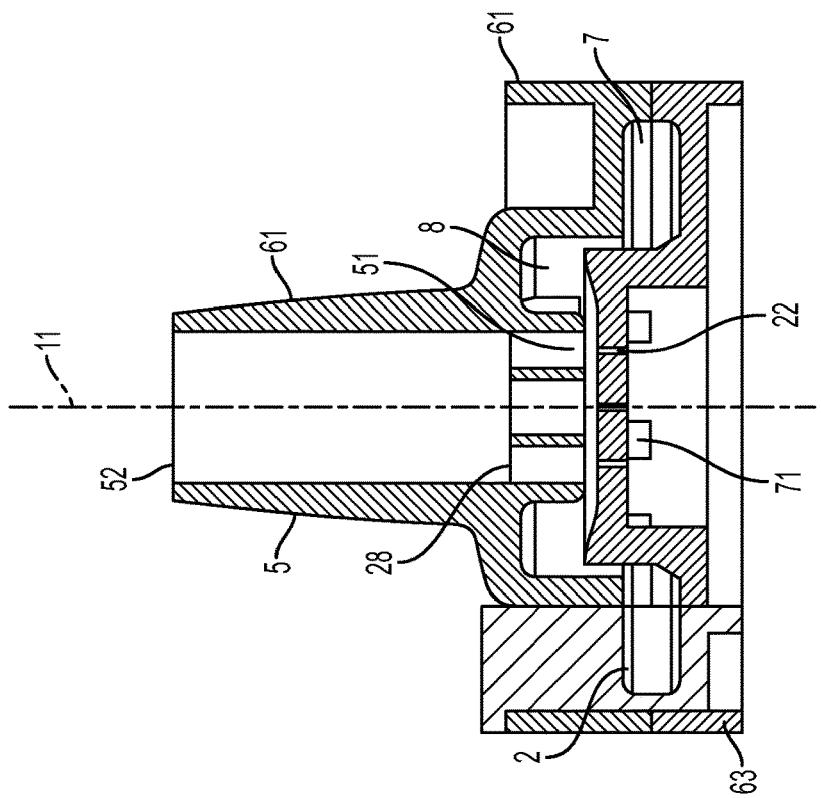
FIGS. 4 and 5 show cross sectional views of a dose delivery device prior to opening of a dose chamber and after opening of the dose chamber, respectively.
Figure 4:
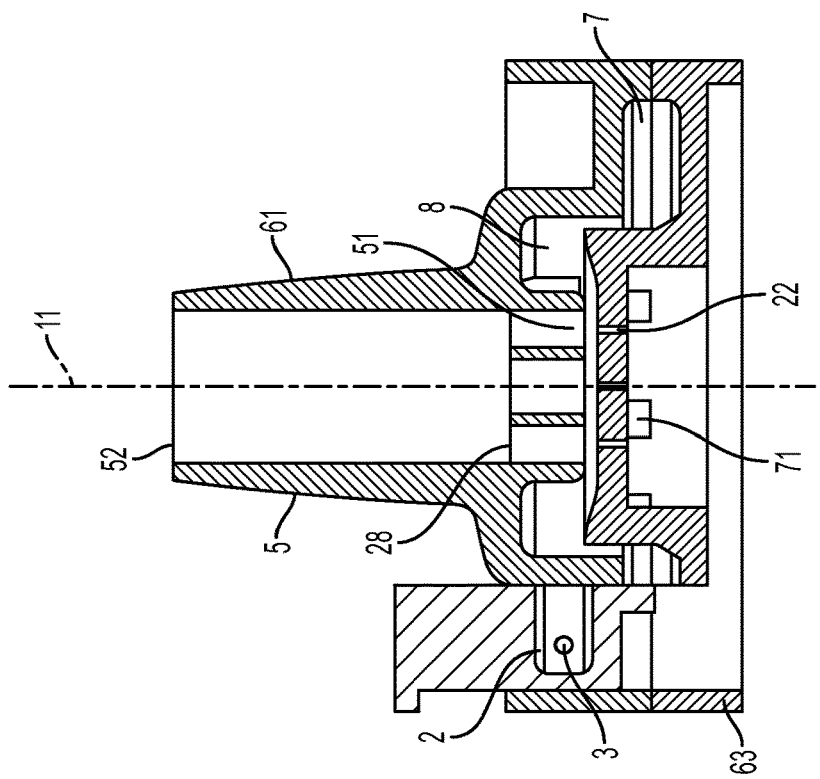
Figure 6:
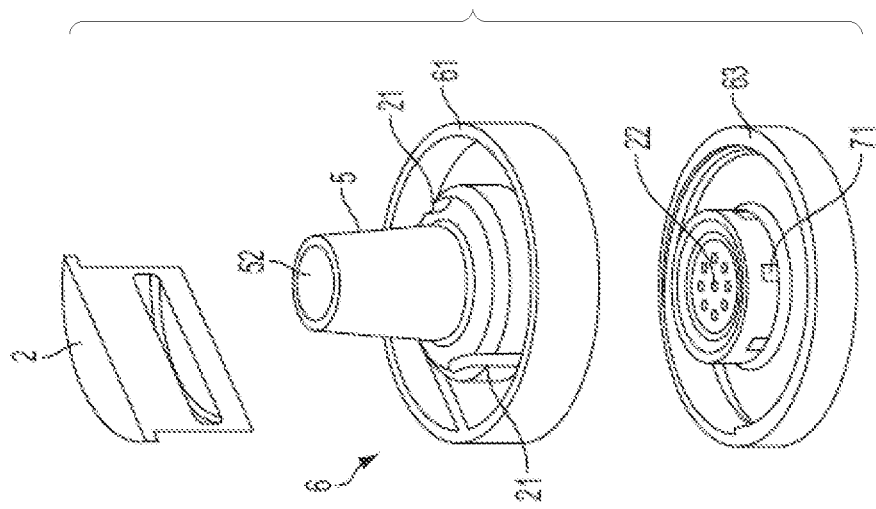
FIG. 6 shows an exploded view of the FIGS. 4 and 5 embodiment.
Figure 26:
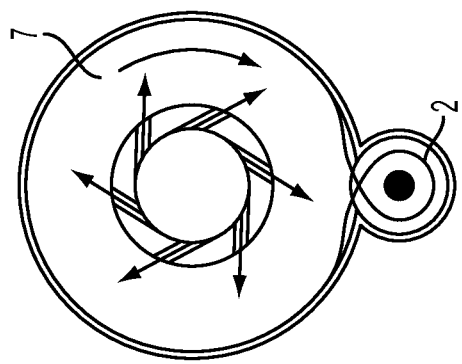
FIGS. 24-26 show illustrative arrangements for arranging a portion of a chamber to provide a dose chamber.
Figure 25:
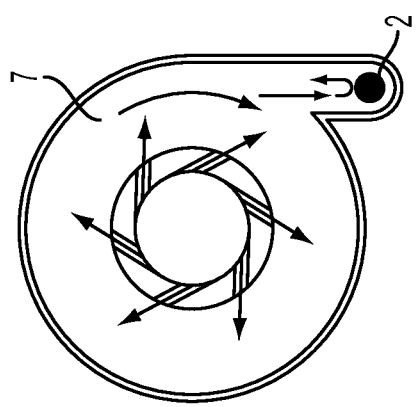
Figure 24:
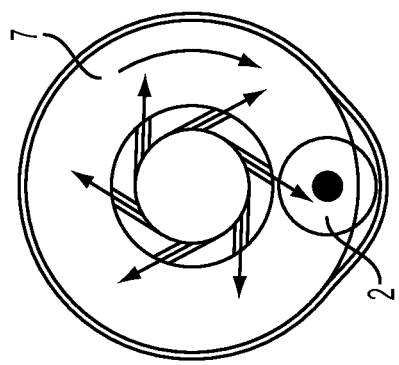

FIGS. 4-6 show cross sectional side views and an exploded view of yet another illustrative embodiment that incorporates one or more aspects of the invention. This embodiment too is similar to that in FIGS. 1 and 2, and in FIG. 3, and common features are not described. However, this embodiment incorporates an aspect of the invention in which a portion of a dispersion chamber (e.g., the first chamber 7) defines a dose chamber 2. That is, in this embodiment, a dose chamber 2 includes a movable element that can be selectively moved into communication with the first chamber 7. FIG. 4 shows a condition in which the dose chamber 2 is closed and the dose 3 is isolated from the first chamber 7 and other external features. FIG. 5 shows a condition in which the dose chamber 2 is moved into communication with the first chamber 7 such that part of the dose chamber 2 forms a part of the first chamber 7. Thus, in this embodiment, a portion of the first chamber 7 may define a dose chamber 2 that can be selectively opened and closed. In some embodiments, a portion of the first chamber 7 that defines the dose chamber 2 may have a size, shape or other configuration that is somewhat different than the remainder of the first chamber 7, e.g., to provide a larger space for holding the dose 3. For example, FIGS. 24-26 show alternate arrangements in which a portion of a first chamber 7 is arranged to define a dose chamber 2. Any of these arrangements may be configured like that in FIGS. 4-6 such that the dose chamber 2 can be selectively opened and closed. In addition, such arrangements for a dose chamber 2 may facilitate filling of the dose chamber with a dose 3, such as by providing a suitable port or other space into which the dose 3 may be loaded.

One difference between this embodiment of FIGS. 4-6 and FIG. 1, is that the middle housing portion 62 is formed as a single part with the lower housing portion 63. As discussed above, the housing 6 may be made of any suitable number or other arrangement of parts. Another feature shown in FIGS. 4-6 which is included with FIGS. 1-3 is a flow straightener 28 near the mouthpiece inlet 51. The flow straightener may reduce air swirling or turbulence as dose-laden air exits the second chamber 8 and travels to the mouthpiece outlet 52. An air stream having reduced turbulence and/or swirl may flow more readily toward a user's lungs, and be less likely to impact walls of the user's mouth, throat, and/or esophagus, where dose may become lodged. The flow straightener 28 shown in FIGS. 4-6 includes multiple openings, arranged in parallel to one another, through which flow that exits the second chamber 8 passes. The parallel orientation and smaller cross-section of the openings of the flow straightener 28 urges flow toward a laminar state, reducing turbulence. It is to be appreciated that other types of flow straighteners may also be used, such as straighteners that include different shapes or lengths of openings, or flow straighteners positioned at different locations within a delivery device. By way of example, a flow straightener 28 may be positioned closer to the mouthpiece outlet 52. In addition, a longer outlet 52 may be provided for increased reduction of air turbulence prior to delivery to a user. Other embodiments may lack a flow straightener altogether, as is to be appreciated.

Figure 7:
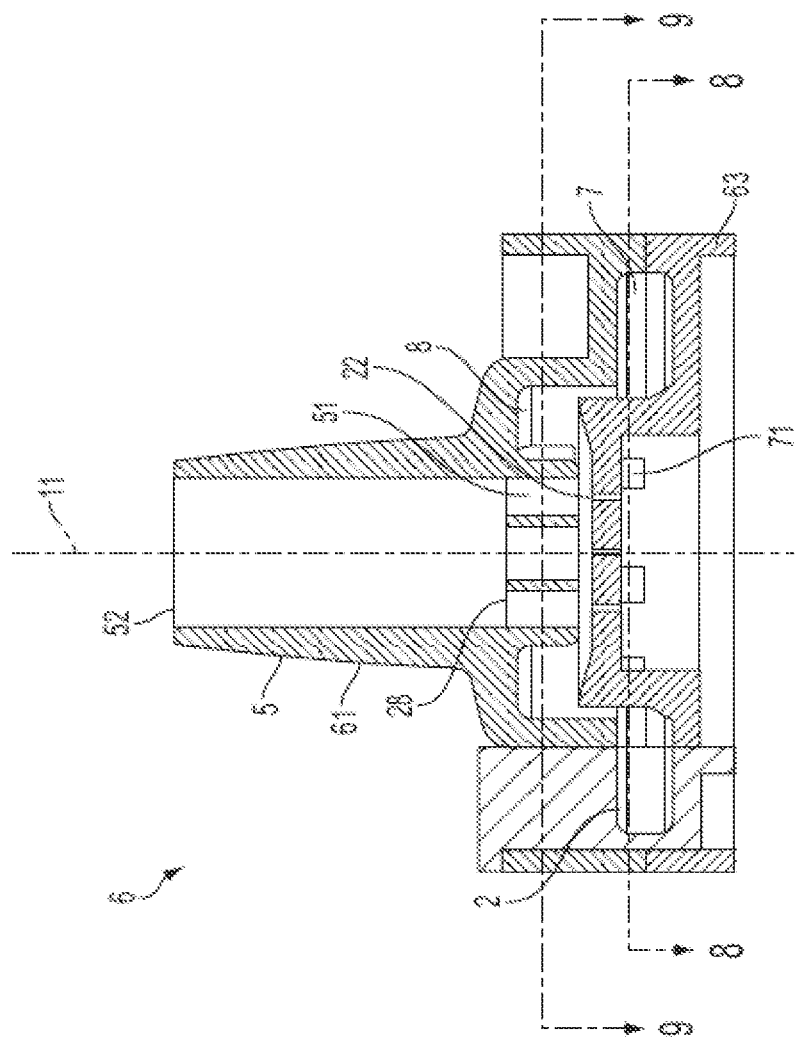
FIG. 7 shows a cross sectional view of the FIGS. 4 and 5 embodiment.
Figure 8:
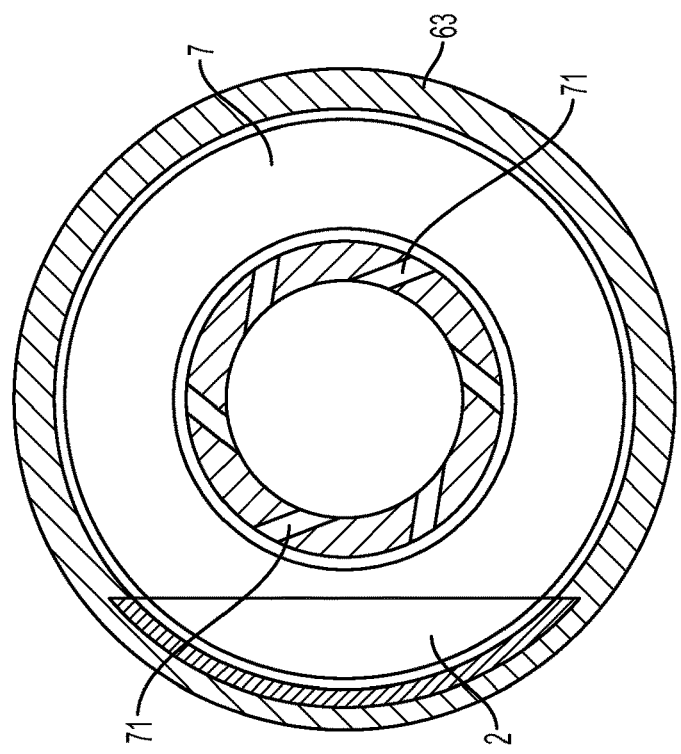
FIG. 8 shows a cross sectional view along the line 8-8 in FIG. 7.
Figure 11:
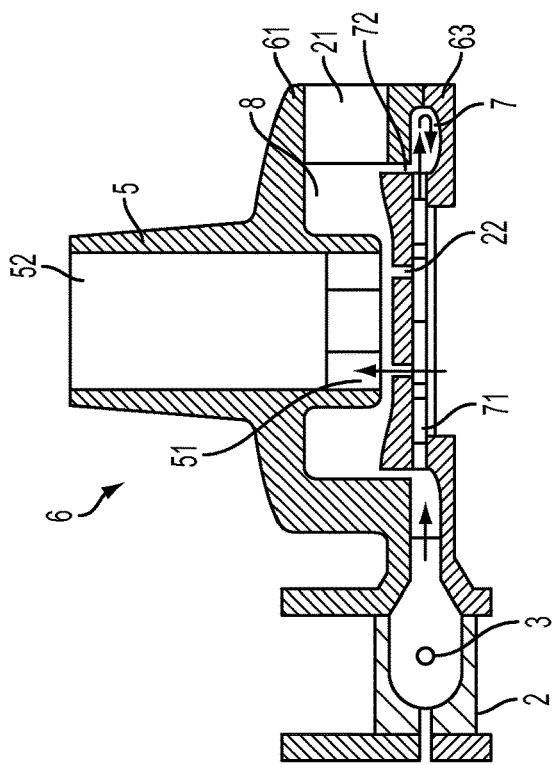
FIG. 11 shows a cross sectional view of a dose delivery device having a dose chamber that is selectively openable and closeable at a side of the device.

Although discussed above, FIGS. 4-6 also show that the first chamber inlet 71 may include multiple openings, e.g., openings that are spaced around an inner periphery of the first chamber 7 and defined by a fan or turbine blade arrangement. Also, FIG. 6 shows that a first bypass inlet 21 may include two or more openings that permit air to enter in a radially inward direction into the second chamber 8. Arrangements for the first chamber inlet 71 and first bypass inlet 21 are shown in more detail in FIGS. 7-9, which show a cross sectional view and section views along the lines 8-8 and 9-9 in FIG. 7. As can be seen in FIG. 8, the first chamber inlet 71 may include multiple channels that introduce air into the first chamber 7 in a generally radially outward direction and in a direction that is generally tangential to circulatory flow in the first chamber 7. In fact, the first chamber inlet 71 may provide the main driving force for circulatory flow in the first chamber 7 about the longitudinal axis 11. However, it is possible to have one or more bypass or other inlets that introduce air into the first chamber 7 to help drive flow in the first chamber 7. As discussed above, the first chamber inlet 71 may also introduce air into the first chamber 7 along a top of the chamber 7 so that flow additionally circulates to flow radially out along the top wall of the chamber 7, downwardly along the outer peripheral wall of the chamber 7, and radially in along the bottom wall of the chamber 7. This circulation combined with circulation about the longitudinal axis 11 may cause the flow in the first chamber to follow a spiral or helical path. FIG. 8 also shows how a portion of the dose chamber 2 forms part of the first chamber 7 (or viewed another way, how a portion of the first chamber 7 forms the dose chamber 2).

Figure 9:
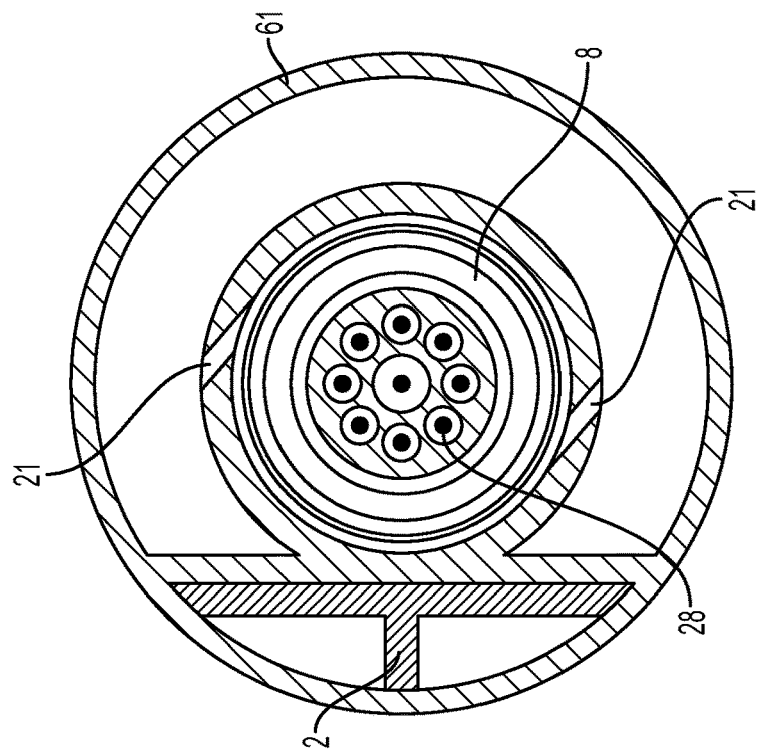
FIG. 9 shows a cross sectional view along the line 9-9 in FIG. 7.

FIG. 9 shows that the first bypass inlet 21 may include two (or more) channels that are arranged to introduce air into the second chamber 8 in a radially inward direction and in a direction generally tangential to the flow in the second chamber 8. Of course, it will be understood that the first bypass inlet 21 may include any suitable number of channels or other openings that are arranged in any suitable way. FIG. 9 also shows a section view of a flow straightener 28 that in this embodiment includes nine parallel channels. As discussed above, the flow straightener 28 may have other suitable arrangements, including any suitable number of channels or other features, such as baffles, fins, walls, etc.

Figure 10:
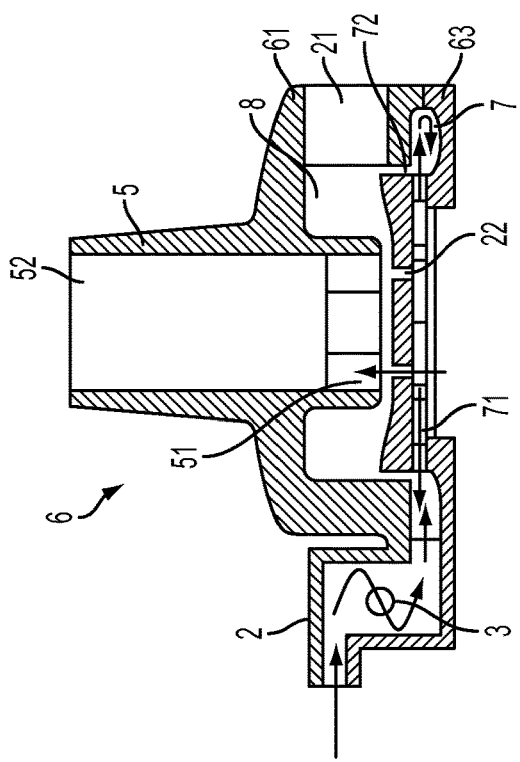
FIG. 10 shows a cross sectional view of a dose delivery device having a dose chamber including a swirl chamber feature.
Figure 13:
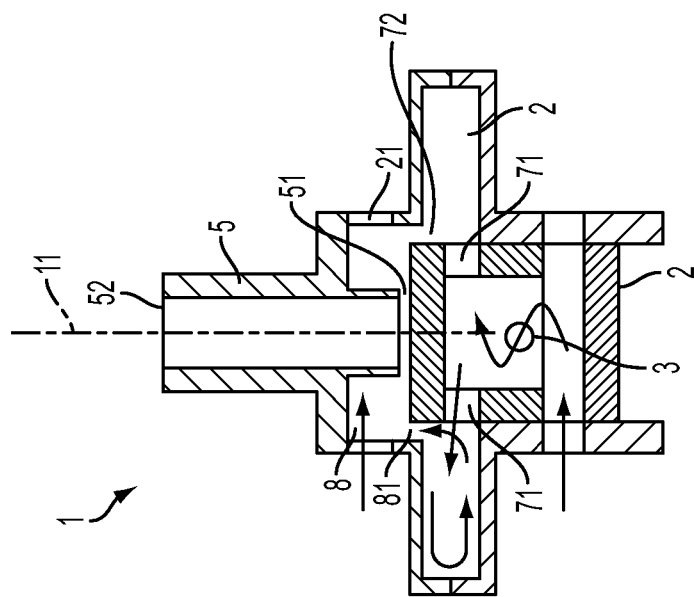
FIG. 13 shows a cross sectional view of a dose delivery device having a dose chamber that is selectively openable and closeable within the device.
Figure 12:
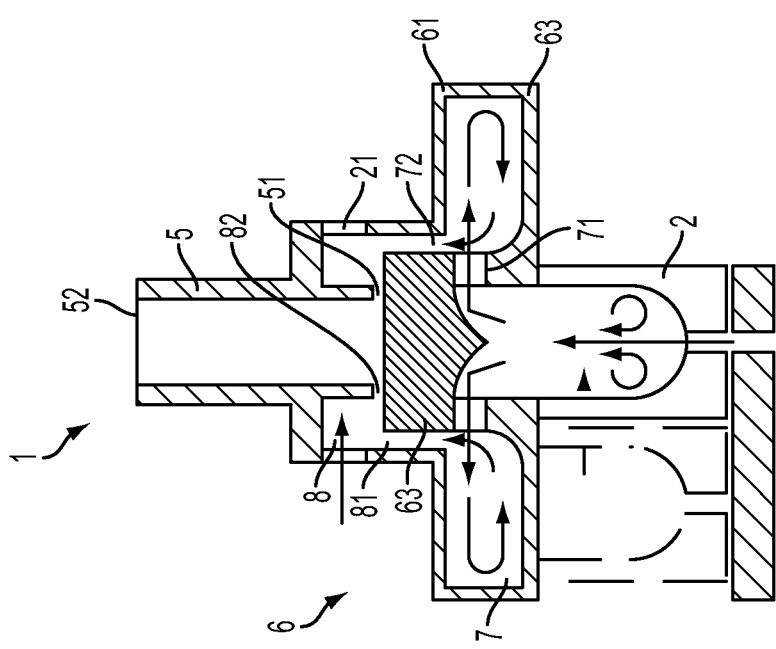
FIG. 12 shows a cross sectional view of a dose delivery device having a dose chamber that is selectively openable and closeable at a bottom of the device.

FIG. 10 shows another illustrative embodiment that is similar to prior embodiments. One difference in the FIG. 10 embodiment is that the dose chamber 2 is formed by part of the housing 6, specifically by portions of the upper and lower housing portions 61 and 63. In this embodiment, the dose chamber 2 itself may be arranged to help disperse the dose 3, e.g., by functioning as a swirl chamber into which incoming air is admitted tangentially to a cylindrically shaped dose chamber 2. The dose chamber 2 may be made selectively openable and closable, such as by allowing for rotation or translation of the dose chamber 2 relative to the remainder of the housing 6. Swirling flow in the dose chamber may help to disperse the dose 3 that is provided to the first chamber 7 for further dispersion or other treatment. FIG. 11 shows a similar embodiment with one difference being that the dose chamber 2 can be selectively opened and closed by moving an element upwardly and downwardly relative to the housing 6. FIG. 11 shows the dose chamber 2 in an open configuration in which air may be admitted into a left side of the chamber 2 to carry dose 3 into the first chamber 7. However, with the dose chamber 2 moved upwardly relative to the housing 6, the dose chamber 2 may be closed between opposed walls of the housing 6. Arrangements like that in FIGS. 10 and 11 may help meter dose into the first chamber 7, since the dose chamber 2 may be configured to circulate dose 3 in the dose chamber 2 or otherwise meter the delivery of dose from the dose chamber 2.

FIG. 12 shows another embodiment that includes a dose chamber arrangement similar to that in FIG. 11. However, in this embodiment of FIG. 12, the dose chamber 2 is located on a lower side of the first chamber 7 and is movable horizontally relative to the housing 6. A closed position of the dose chamber 2 is shown in dashed line in FIG. 12 where the dose chamber 2 is captured between opposed walls of the lower housing portion 63, whereas the open position of the dose chamber 2 is shown in solid line. Circulatory flow in the first chamber 7 is shown clearly in FIG. 12 with flow entering the first chamber 7 via the first chamber inlet 71 entering along a top of the first chamber 7, turning away from the first chamber outlet 72 along the outer periphery of the first chamber 7, and returning radially inwardly along the bottom of the first chamber 7 toward the first chamber outlet 72. This view also shows how flow exiting the first chamber 7 crosses the inlet flow into the chamber 7.

FIG. 13 shows yet another embodiment in which a dose chamber 2 is movable along a longitudinal axis 11 of the delivery device 1 to open and close the dose chamber 2. In this arrangement, the dose chamber 2 may include openings that form the first chamber inlet 71 when in the open position shown in FIG. 13. As will be understood, the dose chamber 2 may be moved downwardly relative to the lower housing portion 63 to close the dose chamber 2. FIG. 13 helps to illustrate that not all embodiments need incorporate all aspects of the invention. For example, in this embodiment, the flow into the first chamber via the first chamber inlet 71 enters near a bottom of the first chamber 7 rather than near a top of the chamber 7. Of course, the dose chamber 2, housing 6 and/or other components could be arranged to ensure that air enters near a top of the chamber 7, if desired. Also, in this embodiment, the second chamber 8 does not include a concave depression opposite the mouthpiece inlet 51, although such a depression may be provided.

FIGS. 14-16 shows cross sectional views and an exploded view of yet another embodiment that incorporates one or more aspects of the invention. In this embodiment, the housing 6 includes an upper housing portion 61, a middle housing portion 62, a lower housing portion 63 and a cover 64. The lower housing portion 63 and the cover 64 cooperate to form the first chamber 7, which can be selectively opened and closed by movement of the middle housing portion 62 relative to the lower housing portion 63. Specifically, the middle housing portion 62 includes a seal **62*b* that can be moved between a closed position shown in FIG. 14** in which the first chamber 7 and the first chamber inlet and outlet 71, 72 are closed, and an open position shown in FIG. 15 in which the first chamber 7 and the first chamber inlet and outlet 71, 72 are open. Movement of the middle housing portion 62 relative to the lower housing portion 63 can be caused by pushing down on the upper housing portion 61, which contacts a plate portion 62a of the middle housing portion 62 and pushes the middle housing portion 62 downwardly relative to the lower housing portion 63. Such movement may be effected by a threaded engagement of the upper and lower housing portions 61 and 63 and relative rotation of the housing portions 61, 63. The cover 64 may allow for loading of a dose 3 into the first chamber 7, e.g., by having the housing portions 61, 62, 63 arranged in the relative positions shown in FIG. 14, and inverting the housing 6 from the position shown in FIG. 14 so the exposed first chamber 7 is facing upwardly. With the dose 3 placed in the first chamber 7, the cover 64 may be placed over the first chamber 7 to close the chamber 7. Thus, the first chamber may, in this and other embodiments, serve as a dose chamber 2 and a dispersion chamber.

Figure 15:
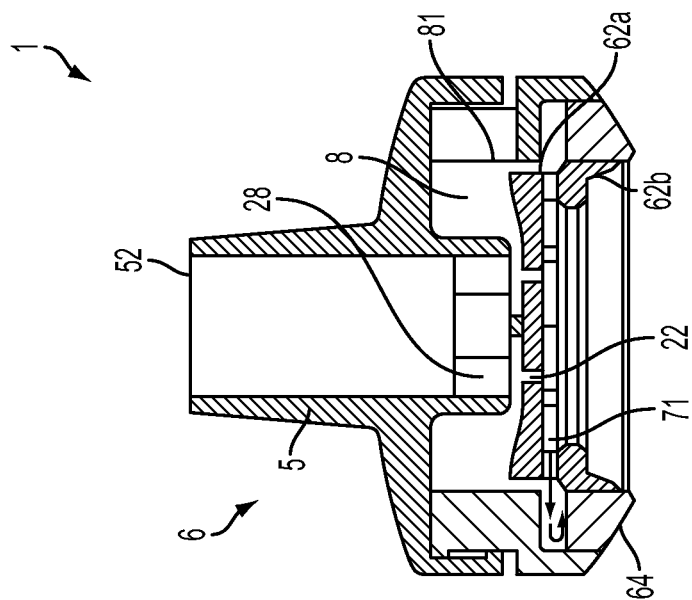
FIGS. 14 and 15 show cross sectional views of a dose delivery device prior to opening of a first chamber and after opening of the first chamber, respectively.
Figure 14:
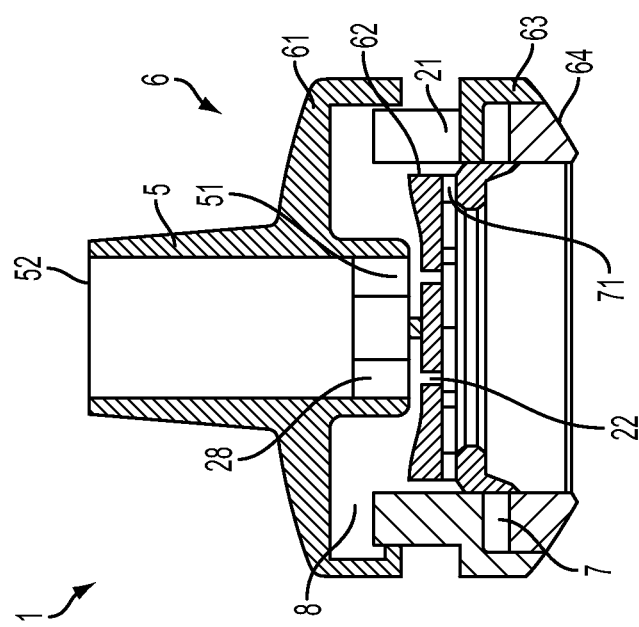
Figure 17:
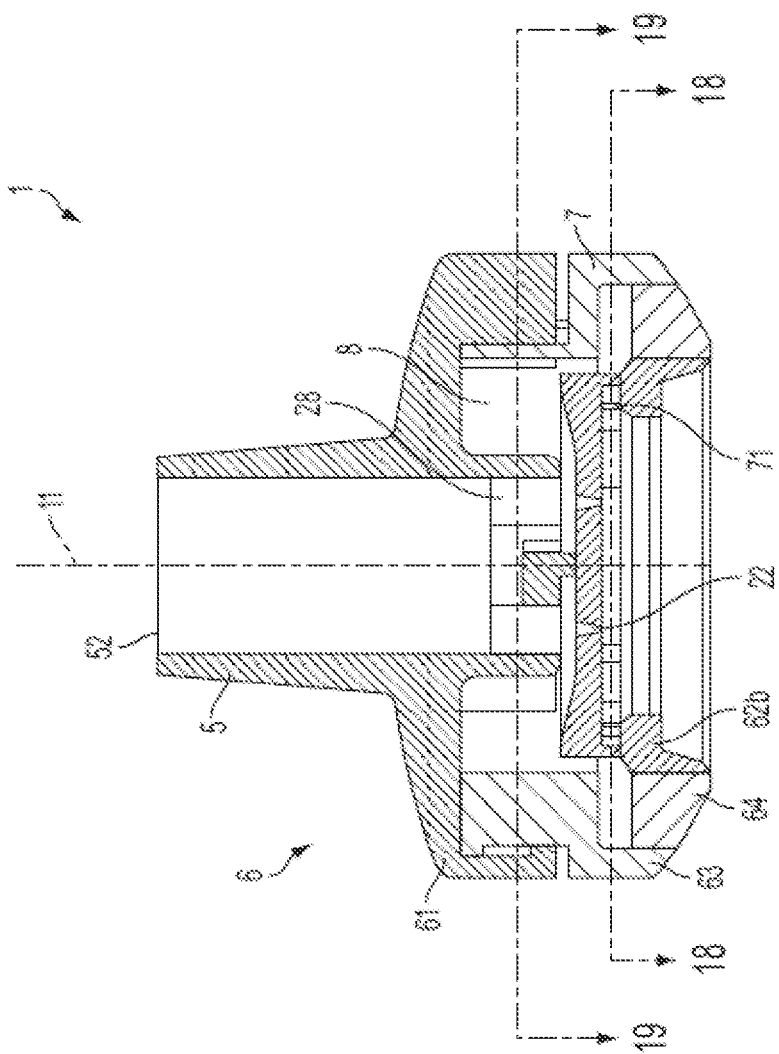
FIG. 17 shows a cross sectional view of the FIGS. 14 and 15 embodiment.
Figure 16:
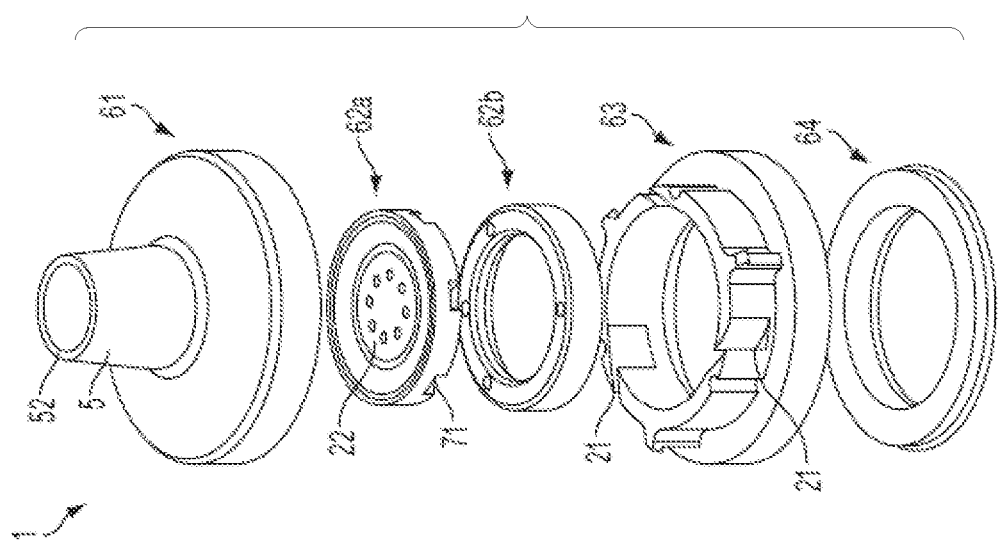
FIG. 16 shows an exploded view of the dose delivery device of FIGS. 14 and 15.
Figure 19:
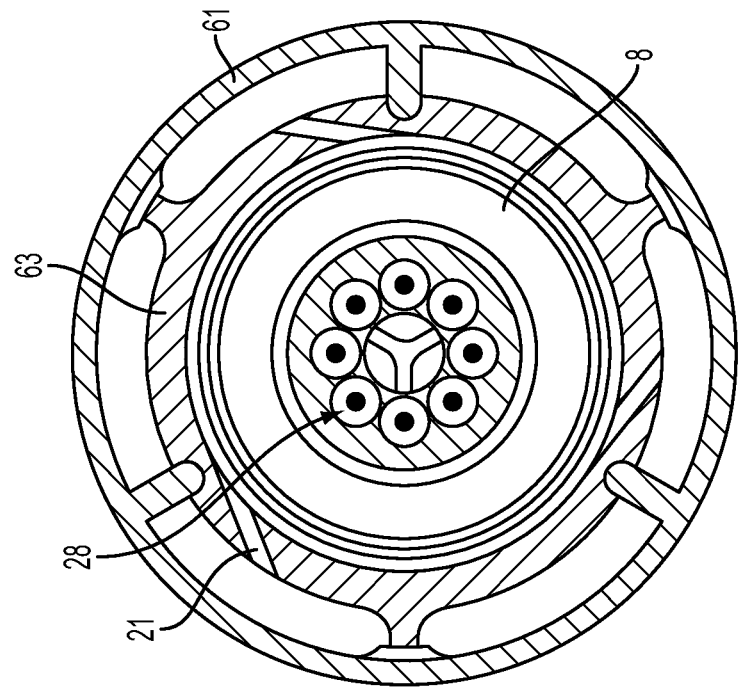
FIG. 19 shows a cross sectional view along the line 19-19 in FIG. 17.
Figure 18:
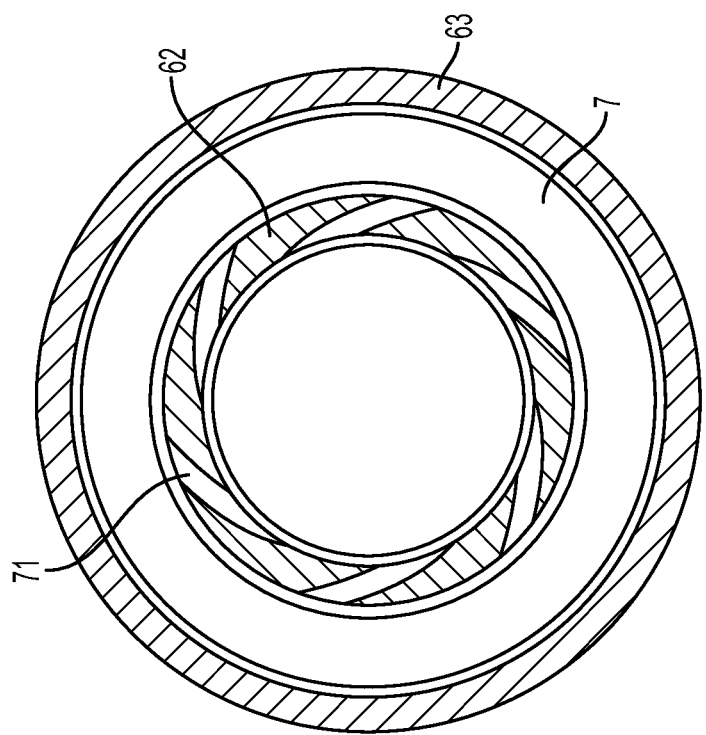
FIG. 18 shows a cross sectional view along the line 18-18 in FIG. 17.

FIGS. 17-19 show a cross sectional view and section views of the FIG. 14-16 embodiment along the lines 18-18 and 19-19 in FIG. 17. As can be seen in FIG. 18, the first chamber inlet 71 is formed in the middle housing portion 62 and may include multiple channels that introduce air into the first chamber 7 in a generally radially outward direction and in a direction that is generally tangential to circulatory flow in the first chamber 7. The first chamber inlet 71 may provide the main driving force for circulatory flow in the first chamber 7 about the longitudinal axis 11. The first chamber inlet 71 may also introduce air into the first chamber 7 along a top of the chamber 7 so that flow additionally circulates to flow radially out along the top wall of the chamber 7, downwardly along the outer peripheral wall of the chamber 7, and radially in along the bottom wall of the chamber 7. This circulation combined with circulation about the longitudinal axis 11 may cause the flow in the first chamber to follow a spiral or helical path.

FIG. 19 shows that the first bypass inlet 21 is formed in the lower housing portion 63 and may include three (or more) channels that are arranged to introduce air into the second chamber 8 in a radially inward direction and in a direction generally tangential to the flow in the second chamber 8. Of course, it will be understood that the first bypass inlet 21 may include any suitable number of channels or other openings that are arranged in any suitable way, including introducing bypass air in a radially outward direction similar to the first chamber inlet 71 in some embodiments above. FIG. 19 also shows a section view of a flow straightener 28 that in this embodiment includes nine parallel channels. As discussed above, the flow straightener 28 may have other suitable arrangements, including any suitable number of channels or other features, such as baffles, fins, walls, etc.

Figure 21:
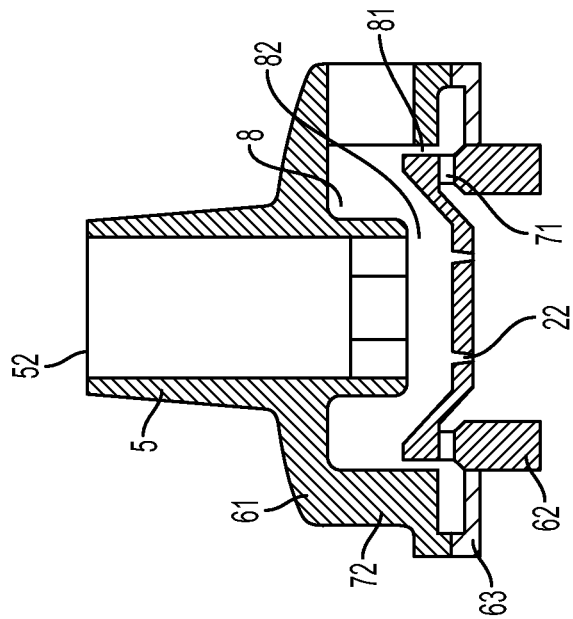
FIGS. 20 and 21 show cross sectional views of a dose delivery device prior to opening of first and second chambers and after opening of the first and second chambers, respectively.
Figure 20:
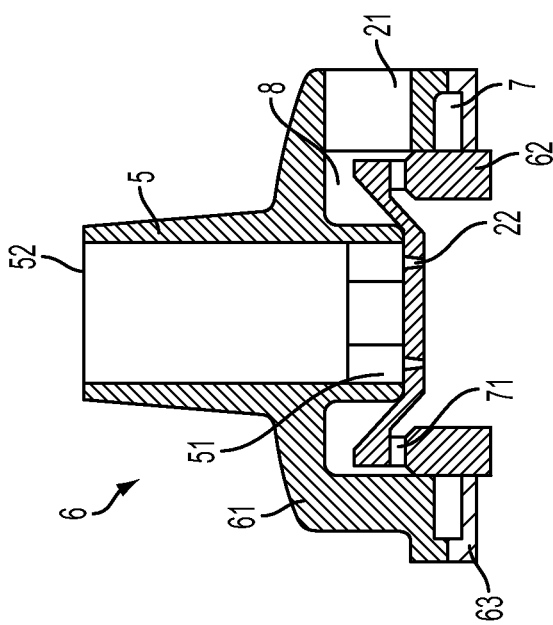
Figure 23:
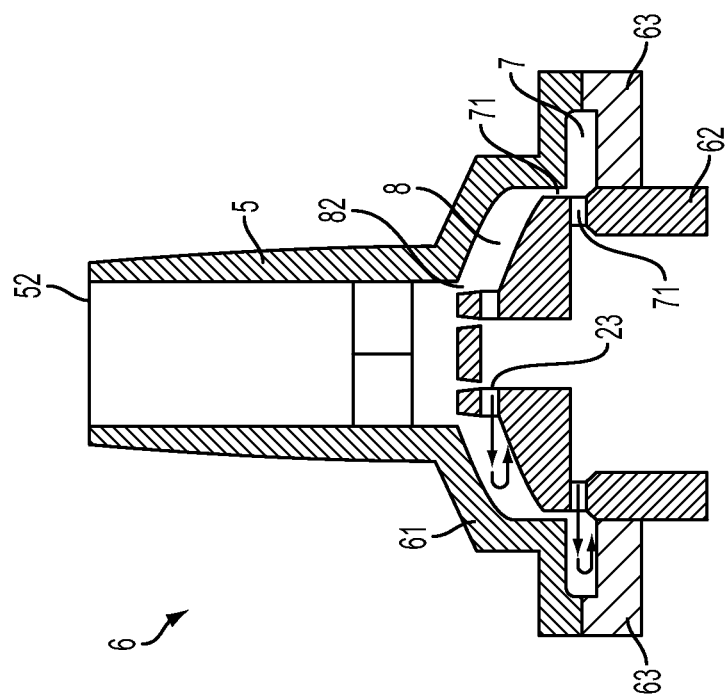
FIGS. 22 and 23 show cross sectional views of a dose delivery device prior to opening of first and second chambers and after opening of the first and second chambers, respectively.
Figure 22:
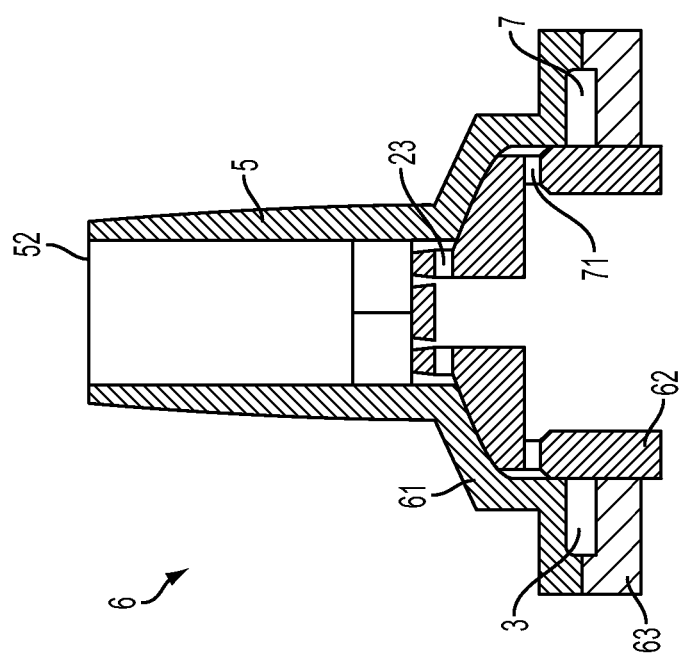

FIGS. 20 and 21 show cross sectional views of yet another illustrative embodiment of a dose delivery device 1. In this embodiment, the housing 6 includes an upper housing portion 61, a middle housing portion 62 and a lower housing portion 63. The middle housing portion 62 is movable relative to the upper and lower housing portions 61, 63 so that in the position shown in FIG. 20, the first chamber 7 (which may contain a dose 3) may be closed. However, when the middle housing portion 62 is moved to the position shown in FIG. 21, the first chamber 7 may be opened. As a result, dose that is contained in the first chamber 7 may be entrained into air flow, e.g., as a user inhales from the mouthpiece outlet 52. This embodiment may be modified to permit the second chamber 8 to be closed as well with the middle housing portion 62 in the position shown in FIG. 20 (e.g., by modifying the shape of the middle housing portion 62 to block the first chamber inlet 71 and bypass inlet 21). This arrangement may be useful, for example, when the first and second chambers 7, 8 contain different materials that are isolated from each other prior to use of the device 1, but are mixed together when delivering the dose materials to a user.

FIGS. 22 and 23 show cross sectional views of another dose delivery device that is similar in some respects to that in FIGS. 20 and 21. In this embodiment, the housing 6 includes an upper housing portion 61, a middle housing portion 62 and a lower housing portion 63. The middle housing portion 62 is movable relative to the upper and lower housing portions 61, 63 so that in the position shown in FIG. 22, the first chamber 7 (which may contain a dose 3) may be closed. In addition, the second chamber 8 may not exist at all in the configuration shown in FIG. 22, although the upper and middle housing portions 61 and 62 could be modified to provide for a second chamber 8 that could be closed with the middle housing portion 62 in the position shown in FIG. 22, which may allow for storage of dose in the second chamber 8. However, when the middle housing portion 62 is moved to the position shown in FIG. 23, the first chamber 7 may be opened. As a result, dose 3 that is contained in the first chamber 7 may be entrained into air flow, e.g., as a user inhales from the mouthpiece outlet 52. Also shown in FIGS. 22 and 23 is that the second chamber 8 includes a bypass inlet 23 that is arranged to admit air into the second chamber 8 in a radially outward direction. Similar to other bypass inlet arrangements discussed above, the bypass inlet 23 may drive circulatory flow in the second chamber 8, if desired. Thus, in this arrangement, both the first and second chambers 7, 8 may have bypass inlets that direct air into the chambers 7, 8 in a radially outward direction. Of course, other bypass inlet arrangements are possible, such as those that direct air into either of the chambers 7, 8 from any suitable direction. As also shown in FIG. 23, the bypass inlet 23 may drive circulatory flow such that incoming flow into the second chamber 8 flows near a top of the second chamber 8, flows downwardly away from the second chamber outlet 82 along an outer peripheral wall of the second chamber 8, and then flows radially inwardly toward second chamber outlet 82. It should also be appreciated that the embodiment of FIGS. 22 and 23 (as well as other embodiments) may incorporate any suitable aspects of the invention. For example, the embodiment of FIGS. 22 and 23 may include a concave depression opposite the mouthpiece inlet 51, a dose chamber arrangement, bypass inlets, and/or other features, such as those included in the FIG. 10 embodiment.

While aspects of the invention are described independently herein (at least to some extent), it should be understood that synergistic or other advantageous effects may be realized by the combination of various aspects of the invention together. For example, providing bypass air into a second chamber in combination with a device that includes two dispersion chambers that provide for circulatory flow may provide particularly effective dose dispersion and metering characteristics. In another example, swirl chambers may work best when there is adequate outer surface area to allow consistent particle to wall collisions. Large agglomerates can disrupt circulation and promote sedimentation that adversely affects particle to wall collisions. The larger first chamber may be sized to provide suitable area to breakdown large agglomerate and meter particles of a predetermined size to the smaller $2^{nd}$ chamber for further breakdown into respirable sizes. As another example, a first chamber, second chamber, and/or a space or other passageway connecting first and second chambers may include one or more bypass inlets that introduce air from an inside, outside or other location with respect to the chamber or passageway, may include no bypasses, and so on.

Air passageways in the delivery device may be configured to accomplish different effects. By way of example, the first chamber inlet 71 may be oriented to create swirling air patterns within the first chamber, which may help to entrain powdered dose. Other flow channels, such as chamber outlets and/or bypass inlets may, additionally or alternatively, be configured to create further air swirling and mixing within the first and second chambers 7, 8 of the delivery device. This may serve to further mix and de-agglomerate any powdered dose before delivering the dose to a user. It is to be appreciated that the orientation of air passageways illustrated with respect to the illustrative embodiments described herein are but one set of possible orientations, and that others are also possible and contemplated.

Passageways, channels and other features of the device 1 may be sized to control flow rates and/or volumes through particular portions of a delivery device. By way of example, the first chamber outlet 72 may be smaller in cross-section or other size than either of the bypass inlets 21 and 22. This may promote a greater volume of flow through each of the bypass inlets than through the first chamber 7, which may help meter the flow of dose-laden air through the device, or control the rate of dose metering from the first chamber 7. The relative size of chamber inlet 71, outlet 72, and/or bypasses 21, 22 may be modified to adjust the rate at which dose is metered, according to some embodiments.

A barrier used to enclose a dose, whether in the form of a dose chamber 2 or a enclosure for all or part of the device 1, may be formed of various materials. According to some embodiments, a barrier may include an aluminum foil that is substantially impervious to light and moisture, although in other embodiments, a barrier may be permeable to some degree of moisture and light. The barrier may be readily adhered to other barriers, such as for foil-on-foil embodiments described herein, or to other structures of a delivery device, that are often formed of plastic. Adhesives, heat weld, friction welds, and other fastening techniques may be used to affix barriers and to provide a seal between the barrier and mating structure. For example, a layer of barrier material may be affixed to a portion of the housing 6, e.g., to close the mouthpiece outlet 52, to cover a bottom portion of the housing 6, etc. In other embodiments, the entire device may be enclosed by a barrier, such as a bag, pouch or other structure that surrounds the device 1.

In use, with the delivery device readied to deliver dose (e.g., by opening a dose chamber and/or other flow channels in the device 1), a user inhales through the device outlet to pull air through the device. Air that enters through the first chamber inlet 71 may entrain, meter, breakdown or otherwise disperse dose and then pass to the second chamber 8 for further dispersion of the dose. Air provided to the second chamber 8 by the bypass inlets 21 and/or 22 may help disperse the dose, as discussed above, and the dispersed dose may move to the device outlet The flow of air through the first and/or second chamber may cause dose therein to be pushed outwardly against the outer peripheral wall of the chamber and may spread the dose evenly about the wall. Air may then flow across the surface of the dose, entraining particles of the dose as the flow progresses about the chamber. Entrained particles may tumble about the chamber and be broken down in to smaller particles for improved delivery. Additionally, larger particles entrained within the flow may have too much momentum to turn or otherwise move toward the chamber outlet, and may continue movement in the chamber to become later entrained in the flow. In this respect, the larger particles may be circulated in the chamber to be de-agglomerated into smaller particles or may remain indefinitely within the chamber.

Single dose delivery devices may be configured for one time use, or may be configured for multiple uses. By way of example, the first chamber 7 may function as a dose chamber 2 that is exhausted after a single user. According to other embodiments, the device may be configured to receive replaceable or rechargeable dose chambers. It is to be appreciated that these are but two examples of ways in which a device may be configured, and that others are possible and are also contemplated. By way of example, some embodiments may not include a separate dose chamber capsule, but instead have a dose chamber that is incorporated into the housing(s) of the delivery device itself.

It is to be appreciated that although various embodiments of the delivery devices are discussed and illustrated herein as a single dose device, that a plurality of any of the dose chambers may be incorporated into a device that may deliver multiple doses. Incorporating multiple dose chambers into a common device may allow some features of a delivery device to be shared among different dose chambers. By way of example, a multi-dose device may include a common outlet that is used to deliver, sequentially, doses from each of the dose chambers to a subject, when needed. Other features may be shared among the different dose chambers of a common, multi-dose device, such as a single actuation button and/or punch that is moved sequentially into registration with each dose chamber to move an opening mechanism between a first and second position to ready a dose for delivery, or a cassette is moved into registration with the punch. Additionally or alternatively, a multi-dose configuration may reduce the overall cost per dose to be delivered from a delivery device.

Delivery devices may also include multiple dose chambers that are opened to expose different doses to a common air pathway for delivery. For instance, some drugs that might be delivered include components that should not be mixed until the components are delivered to a user. In such instances, or for other types of combination therapies, two or more dose chambers may be opened (e.g., the first and second chambers 7, 8) to provide doses to a user at a common time, either through a common airway where the different doses are mixed prior to delivery, or through different air pathways.

In some embodiments, the devices, systems and methods may be free of secondary packaging to facilitate rapid and easy delivery of the dose when the dose needs to be delivered as fast as possible under a stressful circumstance, such as in an emergency situation.

Embodiments described herein may be configured for passive or active applications, or a combination of passive and active fluid administration. For example, each of the embodiments described herein may include use of a compressed fluid to assist in dispersing the dose, i.e., in an active application where fluid flow in the device is driven by an energy source other than a user's inhalation.

The devices, systems and methods described herein may be used to deliver materials, other than a drug/medicament, to the body. The materials may be delivered through the mouth and/or nose and into the oral cavity, nasal cavity, and/or to the lungs. Materials that are intended to be delivered into the oral cavity include, for example, nutritional compositions (such as sugars, candy, food, vitamins, and quick energy supplements in liquid and/or powder (e.g., nanoparticles) form) and non-nutritional compositions (such as flavorants (e.g., esters)). Other materials that may be delivered into the oral cavity include those used for oral hygiene and dental treatment (e.g., breath fresheners, fluoride treatments, teeth whiteners, antibacterial compositions, mouthwashes). Drugs and related compositions (such as anesthetics, therapeutic markers, salt or saline-based therapies) may also be delivered into the oral cavity. Materials that the may be inhaled into the lungs include, for example, drugs (e.g., for treating asthma, bronchitis, diabetes, pneumonia) and therapeutic markers (such as dyes, scanning agents, radio labeling or tagging agents, UV labeling agents, contrasts agents in liquid and/or powder (e.g., nanoparticles) form). In this respect, it is to be appreciated that any of the above materials may be used in the devices, systems, and methods described herein in place of drug(s)/medicaments. It is also to be appreciated that the terms "dose", "drug" and "medicament" are used interchangeable herein, and include any of the foregoing compositions and any others, whether in powder, liquid or other form, that may be delivered to a human or animal for therapeutic, diagnostic, or other effect. In certain aspects, the delivery device is configured for use with other entranceways into a human or animal body, whether naturally formed or created otherwise, and with aspects of the human or animal body other than the respiratory system. Although the embodiments described incorporate air as the fluid for delivering the medicament, other fluids are contemplated as should be apparent to one of skill in the art.

Although embodiments are described as including a "mouthpiece," it should be understood that a "mouthpiece" as used herein refers to an element that is downstream of a dose chamber and is intended to deliver an air/dose combination toward an ultimate outlet located at or near a user's mouth, nose or other receiving area. Thus, a "mouthpiece" need not necessarily be intended for contact with a human mouth. For example, a mouthpiece may be intended for use near a mouth, such as where a user holds the device spaced from the mouth and inhales dose/air emitted from the device outlet. In another embodiment, a mouthpiece may be intended for use with another element that is engaged with the mouthpiece (e.g., at the mouthpiece outlet 52) and is intended for contact with the user's mouth. In one example, a disposable or reusable sleeve or other conduit may be connected to the mouthpiece outlet 52 and provide an extension of the air path of the device beyond the mouthpiece outlet 52. The fact that a dose delivery device is used, or intended for use, with such a sleeve would not render the air flow component downstream of the dose chamber (i.e., the "mouthpiece") that conducts an air/dose combination not a "mouthpiece" as used herein.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A dose delivery device, comprising:
   a housing having an inlet at a first end, an outlet at a second end, and an air path extending between the inlet and the outlet;
   a first chamber having an inlet and an outlet, fluid entering the first chamber via the first chamber inlet being arranged in an inlet direction, the first chamber, the first chamber inlet and the first chamber outlet being arranged such that fluid flowing in an outlet direction to the first chamber outlet is transverse to, and crosses, fluid flowing in the inlet direction;
   a second chamber having an inlet arranged to receive dose entrained air from the first chamber outlet, and an outlet fluidly coupled to the housing to provide dose entrained air to the housing inlet, the second chamber arranged to disperse a dose in the dose entrained air provided to the housing inlet;
   at least one bypass inlet through a side wall of the second chamber to allow air to bypass the first chamber and flow into the second chamber in a generally radially inward direction to induce circulatory flow in the second chamber about a longitudinal axis of the second chamber; and
   a dose chamber arranged to hold a dose.

2. The device of claim 1, wherein a portion of the first chamber defines the dose chamber.

3. The device of claim 1, wherein the first chamber inlet and outlet are selectively openable and closable.

4. The device of claim 1, wherein the first chamber has a toroidal shape and is arranged to cause flow in the first chamber to follow a spiral path.

5. The device of claim 1, wherein the first chamber has a toroidal shape, fluid entering the first chamber via the first chamber inlet moves radially outwardly relative to the toroidal shape, and fluid exiting the first chamber moves axially relative to the toroidal shape.

6. The device of claim 5, wherein the second chamber has a cylindrical shape and receives fluid exiting the first chamber in the axial direction relative to the toroidal shape.

7. The device of claim 6, wherein centers of the toroidal shape of the first chamber and the cylindrical shape of the second chamber are arranged along a longitudinal axis, and the second chamber outlet is located near the longitudinal axis.

8. A dose delivery device, comprising:
   a housing having an inlet at a first end, an outlet at a second end, and an air path extending between the inlet and the outlet;
   a first chamber arranged to provide a dose at a first chamber outlet;
   a second chamber having a cylindrical shape, an inlet arranged to receive a dose from the first chamber outlet, and an outlet fluidly coupled to the housing to provide dose entrained air to the housing inlet, fluid entering the second chamber via the second chamber inlet being arranged in a direction along a longitudinal axis of the cylindrical shape and located near a periphery of the cylindrical shape; and one or more bypass inlets through a side wall of the second chamber and arranged to provide air into the second chamber separately from air received in the first chamber to induce circulatory flow in the second chamber about a longitudinal axis of the second chamber, the bypass inlets being separate from the second chamber inlet.

9. The device of claim 8, wherein the first chamber has a toroidal shape.

10. A dose delivery device, comprising:
a housing having an inlet at a first end, an outlet at a second end, and an air path extending between the inlet and the outlet;
a first chamber arranged to provide a dose at a first chamber outlet; and
a second chamber having an inlet arranged to receive a dose from the first chamber outlet, and an outlet fluidly coupled to the housing to provide dose entrained air to the housing inlet, the second chamber including a concave depression opposite and facing the housing inlet, wherein the concave depression includes at least one opening to direct bypass air toward the housing inlet such that the bypass air bypasses the first chamber and the second chamber and intersects with the dose entrained air at the outlet of the second chamber.

11. A dose delivery device, comprising:
a housing having an inlet at a first end, an outlet at a second end, and an air path extending between the inlet and the outlet;
a first chamber arranged to provide a dose in a fluid flow at a first chamber outlet;
a second chamber having an inlet arranged to receive a dose from the first chamber outlet, and an outlet fluidly coupled to the housing to provide dose entrained air to the housing inlet;
a first bypass inlet arranged to admit air in a generally radially inward direction into the second chamber near the second chamber inlet such that fluid flow from the first chamber outlet into the second chamber inlet is transverse to and intersects with air admitted by the first bypass inlet; and
a second bypass inlet arranged to admit air along a longitudinal axis of the dose delivery device into the second chamber near the second chamber outlet such that fluid flow from the second chamber outlet into the housing inlet is transverse to and intersects with air admitted by the second bypass inlet.

12. The device of claim 11, wherein the first chamber has a toroidal shape having a toroidal shape center, the second chamber has a cylindrical shape having a cylindrical shape center, and wherein the toroidal shape center of the toroidal shape and the cylindrical shape center of the cylindrical shape are located along an air path of the second bypass inlet.

13. A dose delivery device, comprising:
a housing having an inlet at a first end, an outlet at a second end, and an air path extending between the inlet and the outlet;
a first chamber having a toroidal shape arranged to disperse a dose in a fluid flow in the first chamber, an inlet, and an outlet fluidly coupled to the housing to provide dose entrained air to the housing inlet, the first chamber inlet being arranged radially inwardly of the first chamber outlet and near a top surface of the toroidal shape such that the fluid flow enters near the top surface turns away from the first chamber outlet along a periphery of the first chamber, and returns radially inwardly along a bottom of the chamber toward the first chamber outlet, the first chamber inlet and the first chamber outlet being directed along different axes with the first chamber outlet being transverse to the first chamber inlet such that the fluid flow exiting the first chamber crosses the inlet flow into the first chamber from beneath the inlet flow, wherein the top surface of the toroidal shape is located nearer the housing inlet than a bottom surface of the toroidal shape.

14. The device of claim 13, wherein the first chamber outlet is arranged such that fluid flowing in an outlet direction from the first chamber outlet is transverse to, and crosses, fluid flowing into the first chamber via the first chamber inlet in an inlet direction.

15. The device of claim 13, wherein the first chamber defines a dose chamber.

16. The device of claim 13, further comprising a second chamber having an inlet and an outlet, where the second chamber is arranged to receive fluid from the first chamber outlet at the second chamber inlet, and the second chamber outlet provides fluid to the housing inlet.

17. The device of claim 16, further comprising air bypass inlets arranged to admit air into the second chamber in a direction tangential to flow in the second chamber.

18. The device of claim 17, wherein the bypass inlets are arranged to generally direct air in an inward direction into the second chamber.

19. The device of claim 13, wherein the first chamber is arranged to cause flow in the first chamber to follow a spiral path.

20. The device of claim 13, further comprising a dose chamber that is movable to open communication between the dose chamber and the first chamber and allow dose in the dose chamber to enter the first chamber.

21. A dose delivery device, comprising:
a housing having an inlet at a first end, an outlet at a second end, and an air path extending between the inlet and the outlet; and
a first chamber having an inlet and an outlet fluidly coupled to the housing to provide dose entrained air to the housing inlet, fluid entering the first chamber via the first chamber inlet being arranged in a generally radially outward direction, wherein the first chamber inlet is located nearer a top surface of the first chamber than a bottom surface of the first chamber, the first chamber, the first chamber inlet and the first chamber outlet being arranged such that fluid entering via the first chamber inlet is caused to flow radially outwardly along the top surface of the first chamber toward an outer periphery of the first chamber, downwardly along the outer periphery of the first chamber away from the first chamber outlet, and radially inwardly toward the first chamber outlet, the first chamber inlet and the first chamber outlet being directed along different axes with the first chamber outlet being transverse to the first chamber inlet such that the fluid exiting the first chamber crosses an inlet flow into the first chamber from beneath the inlet flow.

22. The device of claim 21, wherein fluid flowing from a bottom of the first chamber toward the first chamber outlet is transverse to, and crosses, fluid flowing into the first chamber from the first chamber inlet.

23. The device of claim 21, wherein the first chamber has a toroidal shape.

* * * * *